United States Patent
Nimkar et al.

(10) Patent No.: US 9,572,956 B2
(45) Date of Patent: Feb. 21, 2017

(54) METHODS AND APPARATUS FOR INSERTING MULTI-LUMEN SPLIT-TIP CATHETERS INTO A BLOOD VESSEL

(71) Applicant: Bard Access Systems, Inc., Salt Lake City, UT (US)

(72) Inventors: Shekhar D. Nimkar, Swampscott, MA (US); Stephen E. Albrecht, South Walpole, MA (US); Paramjith Anand, Ayer, MA (US); Eric Tobin, North Andover, MA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 447 days.

(21) Appl. No.: 14/094,534

(22) Filed: Dec. 2, 2013

(65) Prior Publication Data

US 2014/0088510 A1    Mar. 27, 2014

Related U.S. Application Data

(60) Division of application No. 13/445,713, filed on Apr. 12, 2012, now Pat. No. 8,597,275, which is a division
(Continued)

(51) Int. Cl.
*A61M 25/00*    (2006.01)
*A61M 25/01*    (2006.01)
*A61B 17/34*    (2006.01)

(52) U.S. Cl.
CPC ..... *A61M 25/0102* (2013.01); *A61M 25/0194* (2013.01); *A61B 17/3415* (2013.01)

(58) Field of Classification Search
CPC ............. A61M 2025/0031; A61M 2025/0037; A61M 25/0029; A61M 1/3661; A61M 2025/0034; A61M 25/0194; A61M 25/0102
See application file for complete search history.

(56) References Cited

U.S. PATENT DOCUMENTS 701,075 A     5/1902  McCully
1,696,018 A   12/1928 Scheliberg
(Continued)

FOREIGN PATENT DOCUMENTS

BE    834211    2/1976
CA    1150122   7/1983
(Continued)

OTHER PUBLICATIONS

Haire, et al., Thrombotic Complications of Subclavian Apheresis catheters in Cancer Patients: Prevention With Heparin Infusion, Journal of Clinical Apheresis, 1990, vol. 5, pp. 188-191.
(Continued)

*Primary Examiner* — Aarti B Berdichevsky
(74) *Attorney, Agent, or Firm* — Rutan & Tucker, LLP

(57) ABSTRACT

A catheter assembly includes a catheter, a first intra-catheter stiffener element, and a second intra-catheter stiffener element. The catheter includes a first lumen in fluid communication with a first distal opening and a second lumen in fluid communication with a second distal opening. The first intra-catheter stiffener element is configured for disposition through the first lumen such that a distal end thereof extends distally of the first distal opening, the first intra-catheter stiffener element including a first coupler at a proximal end thereof. The second intra-catheter stiffener element is configured for disposition through the second lumen such that a distal end thereof extends distally of the second distal opening, the second intra-catheter stiffener element including a second coupler at a proximal end thereof.

12 Claims, 7 Drawing Sheets

Related U.S. Application Data of application No. 12/263,141, filed on Oct. 31, 2008, now Pat. No. 8,206,371, which is a continuation of application No. 10/445,731, filed on May 27, 2003, now abandoned.

(56) References Cited

U.S. PATENT DOCUMENTS

| | | |
|---|---|---|
| 1,856,811 A | 5/1932 | Inaki |
| 2,024,982 A | 12/1935 | Scott |
| 2,173,527 A | 9/1939 | Agayoff |
| 2,286,462 A | 6/1942 | Chaffin |
| 2,393,002 A | 1/1946 | Smith |
| 2,748,769 A | 6/1956 | Huber |
| 2,910,981 A | 11/1959 | Wilson et al. |
| 3,144,868 A | 8/1964 | Jascalevich |
| 3,176,690 A | 4/1965 | H'Doubler |
| 3,256,885 A | 6/1966 | Higgins et al. |
| 3,308,822 A | 3/1967 | De Luca |
| 3,416,532 A | 12/1968 | Grossman |
| 3,426,759 A | 2/1969 | Smith |
| 3,460,255 A | 8/1969 | Hutson |
| D217,795 S | 6/1970 | Spaven |
| 3,612,038 A | 10/1971 | Halligan |
| 3,736,939 A | 6/1973 | Taylor |
| 3,805,794 A | 4/1974 | Schlesinger |
| 3,812,851 A | 5/1974 | Rodriguez |
| 3,848,604 A | 11/1974 | Sackner |
| 3,890,977 A | 6/1975 | Wilson |
| 3,929,126 A | 12/1975 | Corsaut |
| 3,935,857 A | 2/1976 | Co |
| 3,995,623 A | 12/1976 | Blake et al. |
| 4,068,659 A | 1/1978 | Moorehead |
| 4,072,146 A | 2/1978 | Howes |
| 4,072,153 A | 2/1978 | Swartz |
| 4,098,275 A | 7/1978 | Consalvo |
| 4,114,625 A | 9/1978 | Onat |
| 4,117,836 A | 10/1978 | Erikson et al. |
| 4,129,129 A | 12/1978 | Amrine |
| 4,134,402 A | 1/1979 | Mahurkar |
| 4,149,535 A | 4/1979 | Volder et al. |
| 4,180,068 A | 12/1979 | Jacobsen et al. |
| D254,444 S | 3/1980 | Levine |
| 4,248,224 A | 2/1981 | Jones |
| 4,276,880 A | 7/1981 | Malmin |
| 4,292,976 A | 10/1981 | Banka |
| 4,299,228 A | 11/1981 | Peters |
| 4,300,550 A | 11/1981 | Gandi et al. |
| 4,309,994 A | 1/1982 | Grunwald |
| 4,327,722 A | 5/1982 | Groshong et al. |
| 4,385,631 A | 5/1983 | Uthmann et al. |
| 4,392,855 A | 7/1983 | Oreopoulos et al. |
| 4,403,983 A | 9/1983 | Edelman et al. |
| 4,405,313 A | 9/1983 | Sisley et al. |
| 4,406,656 A | 9/1983 | Hattler et al. |
| D272,651 S | 2/1984 | Mahurkar |
| 4,431,426 A | 2/1984 | Groshong et al. |
| 4,432,722 A | 2/1984 | Bohan, Jr. et al. |
| 4,432,752 A | 2/1984 | Marlon |
| 4,445,893 A | 5/1984 | Bodicky |
| 4,451,252 A | 5/1984 | Martin et al. |
| 4,453,928 A | 6/1984 | Steiger |
| 4,465,482 A | 8/1984 | Tittel et al. |
| 4,490,138 A | 12/1984 | Lipsky et al. |
| 4,493,696 A | 1/1985 | Uldall et al. |
| RE31,873 E | 4/1985 | Howes |
| 4,531,933 A | 7/1985 | Norton et al. |
| 4,543,087 A | 9/1985 | Sommercorn et al. |
| 4,545,373 A | 10/1985 | Christoudias |
| 4,549,879 A | 10/1985 | Groshong et al. |
| 4,557,261 A | 12/1985 | Rugheimer et al. |
| 4,568,329 A | 2/1986 | Mahurkar |
| 4,568,338 A | 2/1986 | Todd |
| 4,573,476 A | 3/1986 | Ruiz |
| 4,581,012 A | 4/1986 | Brown et al. |
| 4,583,968 A | 4/1986 | Mahurkar |
| 4,583,986 A | 4/1986 | Lapidus |
| 4,601,697 A | 7/1986 | Mammolenti et al. |
| 4,619,643 A | 10/1986 | Bai |
| 4,623,327 A | 11/1986 | Mahurkar |
| 4,626,240 A | 12/1986 | Edelman et al. |
| 4,642,101 A | 2/1987 | Krolikowski et al. |
| 4,643,711 A | 2/1987 | Bates |
| 4,666,426 A | 5/1987 | Aigner et al. |
| 4,668,221 A | 5/1987 | Luther |
| 4,670,009 A | 6/1987 | Bullock |
| 4,675,004 A | 6/1987 | Hadford et al. |
| 4,681,122 A | 7/1987 | Winters et al. |
| 4,681,564 A | 7/1987 | Landreneau |
| 4,681,570 A | 7/1987 | Dalton |
| 4,682,978 A | 7/1987 | Martin et al. |
| 4,687,471 A | 8/1987 | Twardowski et al. |
| 4,692,141 A | 9/1987 | Mahurkar |
| 4,694,838 A | 9/1987 | Wijayarthna et al. |
| 4,701,159 A | 10/1987 | Brown et al. |
| 4,702,917 A | 10/1987 | Schindler |
| 4,706,671 A | 11/1987 | Weinrib |
| 4,713,171 A | 12/1987 | Polaschegg |
| 4,717,379 A | 1/1988 | Ekholmer et al. |
| 4,735,620 A | 4/1988 | Ruiz |
| 4,737,141 A | 4/1988 | Spits et al. |
| 4,737,152 A | 4/1988 | Alchas |
| 4,738,667 A | 4/1988 | Galloway |
| 4,748,808 A | 6/1988 | Hill |
| 4,755,176 A | 7/1988 | Patel |
| 4,769,016 A | 9/1988 | Labianca et al. |
| 4,770,652 A | 9/1988 | Mahurkar |
| 4,772,268 A | 9/1988 | Bates |
| 4,772,269 A | 9/1988 | Twardowski et al. |
| 4,776,841 A | 10/1988 | Catalano |
| 4,777,951 A | 10/1988 | Cribier et al. |
| 4,784,638 A | 11/1988 | Ghajar et al. |
| 4,790,809 A | 12/1988 | Kuntz |
| 4,795,439 A | 1/1989 | Guest |
| 4,801,297 A | 1/1989 | Mueller |
| D300,060 S | 2/1989 | Molgaard-Nielsen |
| 4,804,359 A | 2/1989 | Grunwald et al. |
| 4,808,155 A | 2/1989 | Mahurkar |
| 4,808,163 A | 2/1989 | Laub |
| 4,809,710 A | 3/1989 | Williamson |
| 4,820,265 A | 4/1989 | DeSatnick et al. |
| 4,832,687 A | 5/1989 | Smith, III |
| 4,834,709 A | 5/1989 | Banning et al. |
| 4,842,582 A | 6/1989 | Mahurkar |
| 4,842,592 A | 6/1989 | Caggiani et al. |
| 4,846,814 A | 7/1989 | Ruiz |
| 4,863,441 A | 9/1989 | Lindsay et al. |
| 4,867,742 A | 9/1989 | Calderon |
| 4,892,518 A | 1/1990 | Cupp et al. |
| 4,894,057 A | 1/1990 | Howes |
| 4,895,561 A | 1/1990 | Mahurkar |
| 4,898,591 A | 2/1990 | Jang et al. |
| 4,906,238 A | 3/1990 | Greenfeld et al. |
| 4,925,452 A | 5/1990 | Melinyshyn et al. |
| 4,927,418 A | 5/1990 | Dake et al. |
| 4,935,004 A | 6/1990 | Cruz |
| 4,935,010 A | 6/1990 | Cox et al. |
| 4,935,044 A | 6/1990 | Schoenpflug et al. |
| 4,936,826 A | 6/1990 | Amarasinghe |
| 4,950,232 A | 8/1990 | Ruzicka et al. |
| 4,950,259 A | 8/1990 | Geary et al. |
| 4,951,665 A | 8/1990 | Schneider |
| 4,961,729 A | 10/1990 | Vaillancourt |
| 4,961,731 A | 10/1990 | Bodicky et al. |
| 4,961,809 A | 10/1990 | Martin et al. |
| 4,968,307 A | 11/1990 | Dake et al. |
| 4,969,890 A | 11/1990 | Sugita et al. |
| 4,981,477 A | 1/1991 | Schon et al. |
| 4,985,014 A | 1/1991 | Orejola |
| 4,990,138 A | 2/1991 | Bacich et al. |
| 4,994,027 A | 2/1991 | Farrell |
| 4,995,865 A | 2/1991 | Gahara et al. |
| 5,009,636 A | 4/1991 | Wortley et al. |
| 5,015,230 A | 5/1991 | Martin et al. |

(56) References Cited

U.S. PATENT DOCUMENTS

| | | |
|---|---|---|
| 5,016,640 A | 5/1991 | Ruiz |
| 5,021,044 A | 6/1991 | Sharkawy |
| 5,041,101 A | 8/1991 | Seder et al. |
| 5,041,107 A | 8/1991 | Heil, Jr. |
| 5,049,138 A | 9/1991 | Chevalier et al. |
| 5,053,003 A | 10/1991 | Dadson et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,069,673 A | 12/1991 | Shwab |
| 5,074,841 A | 12/1991 | Ademovic et al. |
| 5,084,013 A | 1/1992 | Takase et al. |
| 5,098,412 A | 3/1992 | Shiu et al. |
| 5,100,395 A | 3/1992 | Rosenberg et al. |
| 5,102,402 A | 4/1992 | Dror et al. |
| 5,106,368 A | 4/1992 | Uldall et al. |
| 5,106,376 A | 4/1992 | Mononen et al. |
| 5,111,829 A | 5/1992 | Alvarez de Toledo |
| 5,112,301 A | 5/1992 | Fenton, Jr. et al. |
| 5,114,423 A | 5/1992 | Kasprzyk et al. |
| 5,117,836 A | 6/1992 | Millar |
| 5,120,299 A | 6/1992 | Lombardi |
| 5,120,304 A | 6/1992 | Sasaki |
| 5,122,125 A | 6/1992 | Deuss et al. |
| 5,125,888 A | 6/1992 | Howard et al. |
| 5,125,904 A | 6/1992 | Lee |
| 5,129,891 A | 7/1992 | Young |
| 5,135,599 A | 8/1992 | Martin et al. |
| 5,139,486 A | 8/1992 | Moss |
| 5,156,592 A | 10/1992 | Martin et al. |
| 5,163,928 A | 11/1992 | Hobbs et al. |
| 5,167,623 A | 12/1992 | Cianci et al. |
| 5,171,216 A | 12/1992 | Dasse et al. |
| 5,171,227 A | 12/1992 | Twardowski et al. |
| 5,178,616 A | 1/1993 | Uemiya et al. |
| 5,188,592 A | 2/1993 | Hakki |
| 5,188,593 A | 2/1993 | Martin |
| 5,190,520 A | 3/1993 | Fenton, Jr. et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,973 A | 3/1993 | Pang et al. |
| 5,197,976 A | 3/1993 | Herweck et al. |
| 5,201,723 A | 4/1993 | Quinn |
| 5,207,648 A | 5/1993 | Gross |
| 5,207,650 A | 5/1993 | Martin |
| 5,209,723 A | 5/1993 | Twardowski et al. |
| 5,209,725 A | 5/1993 | Roth |
| 5,209,742 A | 5/1993 | Venema et al. |
| 5,215,527 A | 6/1993 | Beck et al. |
| 5,221,255 A | 6/1993 | Mahurkar et al. |
| 5,221,256 A | 6/1993 | Mahurkar |
| 5,222,949 A | 6/1993 | Kaldany |
| 5,226,880 A | 7/1993 | Martin et al. |
| 5,234,438 A | 8/1993 | Semrad |
| 5,236,016 A | 8/1993 | Vogelsang et al. |
| 5,242,398 A | 9/1993 | Knoll et al. |
| 5,246,430 A | 9/1993 | MacFarlane |
| 5,250,034 A | 10/1993 | Appling et al. |
| 5,254,084 A | 10/1993 | Geary |
| 5,273,527 A | 12/1993 | Schatz et al. |
| 5,273,534 A | 12/1993 | Knoepfler |
| 5,279,596 A | 1/1994 | Castaneda et al. |
| 5,279,599 A | 1/1994 | Wilk |
| 5,306,240 A | 4/1994 | Berry |
| 5,312,337 A | 5/1994 | Flaherty et al. |
| 5,312,357 A | 5/1994 | Buijs et al. |
| 5,318,517 A | 6/1994 | Reiman |
| 5,322,519 A | 6/1994 | Ash |
| 5,324,274 A | 6/1994 | Martin |
| 5,330,432 A | 7/1994 | Yoon |
| 5,338,308 A | 8/1994 | Wilk |
| 5,342,295 A | 8/1994 | Imran |
| 5,342,386 A | 8/1994 | Trotta |
| 5,346,471 A | 9/1994 | Raulerson |
| 5,348,536 A | 9/1994 | Young et al. |
| 5,350,358 A | 9/1994 | Martin |
| 5,360,397 A | 11/1994 | Pinchuk |
| 5,360,407 A | 11/1994 | Leonard et al. |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,380,290 A | 1/1995 | Makower et al. |
| 5,382,238 A | 1/1995 | Abrahamson et al. |
| 5,389,087 A | 2/1995 | Miraki |
| 5,389,090 A | 2/1995 | Fischell et al. |
| 5,395,316 A | 3/1995 | Martin |
| 5,399,168 A | 3/1995 | Wadsworth, Jr. et al. |
| 5,403,291 A | 4/1995 | Abrahamson |
| 5,405,320 A | 4/1995 | Twardowski et al. |
| 5,405,341 A | 4/1995 | Martin |
| 5,409,463 A | 4/1995 | Thomas et al. |
| 5,417,668 A | 5/1995 | Setzer et al. |
| 5,423,768 A | 6/1995 | Folden et al. |
| 5,431,661 A | 7/1995 | Koch |
| 5,451,026 A | 9/1995 | Smith |
| 5,451,206 A | 9/1995 | Young |
| 5,451,233 A | 9/1995 | Yock |
| 5,458,570 A | 10/1995 | May, Jr. |
| 5,458,582 A | 10/1995 | Nakao |
| 5,462,533 A | 10/1995 | Daugherty |
| 5,472,417 A | 12/1995 | Martin et al. |
| 5,472,432 A | 12/1995 | Martin |
| 5,476,453 A | 12/1995 | Mehta |
| 5,480,380 A | 1/1996 | Martin |
| 5,486,159 A | 1/1996 | Mahurkar |
| 5,489,278 A | 2/1996 | Abrahamson |
| 5,496,292 A | 3/1996 | Burnham |
| 5,496,872 A | 3/1996 | Constancis et al. |
| 5,505,710 A | 4/1996 | Dorsey, III |
| 5,507,723 A | 4/1996 | Keshaviah |
| 5,509,897 A | 4/1996 | Twardowski et al. |
| 5,509,900 A | 4/1996 | Kirkman |
| 5,509,902 A | 4/1996 | Raulerson |
| 5,542,925 A | 8/1996 | Orth |
| 5,545,373 A | 8/1996 | Maziasz et al. |
| 5,556,390 A | 9/1996 | Hicks |
| 5,556,930 A | 9/1996 | Brehm et al. |
| 5,558,635 A | 9/1996 | Cannon |
| 5,562,609 A | 10/1996 | Brumbach |
| 5,562,696 A | 10/1996 | Nobles et al. |
| 5,569,182 A | 10/1996 | Twardowski et al. |
| 5,569,195 A | 10/1996 | Saab |
| 5,571,093 A | 11/1996 | Cruz et al. |
| 5,584,803 A | 12/1996 | Stevens et al. |
| 5,599,304 A | 2/1997 | Shaari |
| 5,599,328 A | 2/1997 | Stevens |
| 5,607,462 A | 3/1997 | Imran |
| 5,624,392 A | 4/1997 | Saab |
| 5,624,413 A | 4/1997 | Markel et al. |
| 5,632,729 A | 5/1997 | Cai et al. |
| 5,637,102 A | 6/1997 | Tolkoff et al. |
| 5,642,270 A | 6/1997 | Green et al. |
| 5,655,867 A | 8/1997 | Gysi et al. |
| 5,662,606 A | 9/1997 | Cimino et al. |
| 5,665,067 A | 9/1997 | Linder et al. |
| 5,674,237 A | 10/1997 | Ott |
| 5,685,867 A | 11/1997 | Twardowski et al. |
| 5,686,867 A | 11/1997 | Sutardja et al. |
| 5,693,030 A | 12/1997 | Lee et al. |
| 5,695,457 A | 12/1997 | St. Goar et al. |
| 5,704,915 A | 1/1998 | Melsky et al. |
| 5,713,849 A | 2/1998 | Bosma et al. |
| 5,713,853 A | 2/1998 | Clark et al. |
| 5,717,216 A | 2/1998 | McCoy et al. |
| 5,718,678 A | 2/1998 | Fleming, III |
| 5,718,692 A | 2/1998 | Schon et al. |
| 5,720,735 A | 2/1998 | Dorros |
| 5,738,649 A | 4/1998 | Macoviak |
| 5,741,329 A | 4/1998 | Agrawal et al. |
| 5,743,873 A | 4/1998 | Cai et al. |

(56) References Cited

U.S. PATENT DOCUMENTS

| | | |
|---|---|---|
| 5,752,939 A | 5/1998 | Makoto et al. |
| 5,769,796 A | 6/1998 | Palermo et al. |
| 5,772,643 A | 6/1998 | Howell et al. |
| 5,776,096 A | 7/1998 | Fields |
| 5,776,111 A | 7/1998 | Tesio |
| 5,785,686 A | 7/1998 | Runge |
| 5,792,094 A | 8/1998 | Stevens et al. |
| 5,792,123 A | 8/1998 | Ensminger |
| 5,797,869 A | 8/1998 | Martin et al. |
| 5,800,384 A | 9/1998 | Russell et al. |
| 5,800,414 A | 9/1998 | Cazal et al. |
| 5,800,516 A | 9/1998 | Fine et al. |
| 5,807,311 A | 9/1998 | Palestrant |
| 5,807,318 A | 9/1998 | St. Goar et al. |
| 5,807,329 A | 9/1998 | Gelman |
| 5,809,897 A | 9/1998 | Powell et al. |
| 5,810,789 A | 9/1998 | Powers et al. |
| 5,814,016 A | 9/1998 | Valley et al. |
| 5,830,184 A | 11/1998 | Basta |
| 5,830,196 A | 11/1998 | Hicks |
| 5,833,671 A | 11/1998 | Macoviak et al. |
| 5,843,048 A | 12/1998 | Gross |
| 5,858,009 A | 1/1999 | Jonkman |
| 5,861,010 A | 1/1999 | Boussignac et al. |
| 5,868,717 A | 2/1999 | Prosl |
| 5,873,865 A | 2/1999 | Horzewski et al. |
| 5,876,366 A | 3/1999 | Dykstra et al. |
| 5,876,426 A | 3/1999 | Kume et al. |
| 5,882,347 A | 3/1999 | Mouris-Laan et al. |
| 5,891,111 A | 4/1999 | Ismael et al. |
| 5,904,670 A | 5/1999 | Schreiner |
| 5,911,715 A | 6/1999 | Berg et al. |
| 5,913,848 A | 6/1999 | Luther et al. |
| 5,916,208 A | 6/1999 | Luther et al. |
| 5,919,160 A | 7/1999 | Sanfilippo, II |
| 5,944,732 A | 8/1999 | Raulerson et al. |
| 5,947,937 A | 9/1999 | Urrutia et al. |
| 5,947,953 A | 9/1999 | Ash et al. |
| 5,957,879 A | 9/1999 | Roberts et al. |
| 5,957,893 A | 9/1999 | Luther et al. |
| 5,957,912 A | 9/1999 | Heitzmann |
| 5,961,486 A | 10/1999 | Twardowski et al. |
| 5,964,796 A | 10/1999 | Imran |
| 5,976,103 A | 11/1999 | Martin |
| 5,976,120 A | 11/1999 | Chow et al. |
| 5,980,551 A | 11/1999 | Summers et al. |
| 5,984,908 A | 11/1999 | Davis et al. |
| 5,989,206 A | 11/1999 | Prosl et al. |
| 5,989,213 A | 11/1999 | Maginot |
| 6,001,079 A | 12/1999 | Pourchez |
| 6,033,382 A | 3/2000 | Basta |
| 6,036,654 A | 3/2000 | Quinn et al. |
| 6,059,771 A | 5/2000 | Balbierz et al. |
| 6,074,374 A | 6/2000 | Fulton |
| 6,086,555 A | 7/2000 | Eliasen et al. |
| 6,090,096 A | 7/2000 | St. Goar et al. |
| 6,099,513 A | 8/2000 | Spehalski |
| 6,103,778 A | 8/2000 | Hyon et al. |
| 6,106,540 A | 8/2000 | White et al. |
| 6,113,572 A | 9/2000 | Gailey et al. |
| 6,117,117 A | 9/2000 | Mauch |
| 6,120,494 A | 9/2000 | Jonkman |
| 6,126,631 A | 10/2000 | Loggie |
| 6,143,013 A | 11/2000 | Samson et al. |
| 6,146,354 A | 11/2000 | Beil |
| 6,146,373 A | 11/2000 | Cragg et al. |
| 6,152,909 A | 11/2000 | Bagaoisan et al. |
| 6,156,016 A | 12/2000 | Maginot |
| 6,161,547 A | 12/2000 | Barbut |
| 6,178,356 B1 | 1/2001 | Chastain et al. |
| 6,180,059 B1 | 1/2001 | Divino, Jr. et al. |
| 6,190,349 B1 | 2/2001 | Ash et al. |
| 6,190,371 B1 | 2/2001 | Maginot et al. |
| 6,193,685 B1 | 2/2001 | Goodin |
| 6,196,996 B1 | 3/2001 | Teirstein |
| 6,206,849 B1 | 3/2001 | Martin et al. |
| 6,210,365 B1 | 4/2001 | Afzal |
| 6,210,380 B1 | 4/2001 | Mauch |
| 6,217,527 B1 | 4/2001 | Selmon et al. |
| 6,224,622 B1 | 5/2001 | Kotzev |
| 6,238,406 B1 | 5/2001 | Ellis et al. |
| 6,264,627 B1 | 7/2001 | Liska et al. |
| 6,273,879 B1 | 8/2001 | Keith et al. |
| 6,280,413 B1 | 8/2001 | Clark et al. |
| 6,280,423 B1 | 8/2001 | Davey et al. |
| 6,287,326 B1 | 9/2001 | Pecor |
| 6,293,927 B1 | 9/2001 | McGuckin, Jr. |
| 6,293,958 B1 | 9/2001 | Berry et al. |
| 6,296,631 B2 | 10/2001 | Chow |
| 6,299,631 B1 | 10/2001 | Shalaby |
| 6,322,551 B1 | 11/2001 | Brugger |
| 6,328,730 B1 | 12/2001 | Harkrider, Jr. |
| 6,342,120 B1 | 1/2002 | Basta |
| 6,361,529 B1 | 3/2002 | Goodin et al. |
| 6,383,172 B1 | 5/2002 | Barbut |
| 6,394,141 B2 | 5/2002 | Wages et al. |
| 6,394,142 B1 | 5/2002 | Woelfel et al. |
| 6,409,700 B1 | 6/2002 | Siegel, Jr. et al. |
| 6,413,228 B1 | 7/2002 | Hung et al. |
| 6,428,513 B1 | 8/2002 | Abrahamson |
| 6,443,922 B1 | 9/2002 | Roberts et al. |
| 6,450,988 B1 | 9/2002 | Bradshaw |
| 6,453,185 B1 | 9/2002 | O'Keefe |
| 6,454,997 B1 | 9/2002 | Divino, Jr. et al. |
| 6,463,335 B1 | 10/2002 | Munch et al. |
| 6,468,287 B1 | 10/2002 | Baugh |
| 6,475,207 B1 | 11/2002 | Maginot et al. |
| 6,475,209 B1 | 11/2002 | Larson et al. |
| 6,478,789 B1 | 11/2002 | Spehalski et al. |
| 6,482,169 B1 | 11/2002 | Kuhle |
| 6,533,763 B1 | 3/2003 | Schneiter |
| 6,565,594 B1 | 5/2003 | Herweck et al. |
| 6,576,001 B2 | 6/2003 | Werneth et al. |
| 6,582,459 B1 | 6/2003 | Lau et al. |
| 6,585,705 B1 | 7/2003 | Maginot et al. |
| 6,592,565 B2 | 7/2003 | Twardowski |
| 6,595,966 B2 | 7/2003 | Davey et al. |
| 6,620,118 B1 | 9/2003 | Prosl et al. |
| 6,638,242 B2 | 10/2003 | Wilson et al. |
| 6,659,134 B2 | 12/2003 | Navis |
| 6,682,498 B2 | 1/2004 | Ross |
| 6,682,519 B1 | 1/2004 | Schon |
| 6,691,625 B2 | 2/2004 | Duncan |
| 6,695,832 B2 | 2/2004 | Schon et al. |
| 6,702,776 B2 | 3/2004 | Quinn |
| 6,712,797 B1 | 3/2004 | Southern, Jr. |
| 6,712,798 B2 | 3/2004 | Constantz |
| 6,719,717 B1 | 4/2004 | Johnson et al. |
| 6,719,749 B1 | 4/2004 | Schweikert et al. |
| 6,723,084 B1 | 4/2004 | Maginot et al. |
| 6,723,114 B2 | 4/2004 | Shalaby |
| 6,730,299 B1 | 5/2004 | Tayot et al. |
| 6,752,827 B2 | 6/2004 | Ross et al. |
| 6,755,851 B2 | 6/2004 | Noda et al. |
| 6,758,836 B2 | 7/2004 | Zawacki |
| 6,786,664 B2 | 9/2004 | Claramunt et al. |
| 6,786,884 B2 | 9/2004 | DeCant, Jr. et al. |
| 6,796,991 B2 | 9/2004 | Nardeo |
| 6,797,107 B1 | 9/2004 | Kotzey |
| 6,808,510 B1 | 10/2004 | DiFiore |
| 6,814,718 B2 | 11/2004 | McGuckin, Jr. et al. |
| 6,819,951 B2 | 11/2004 | Patel et al. |
| 6,821,287 B1 | 11/2004 | Jang |
| 6,824,554 B1 | 11/2004 | Jang |
| 6,835,452 B1 | 12/2004 | Hamerski |
| 6,837,864 B1 | 1/2005 | Bertolero et al. |
| 6,852,079 B2 | 2/2005 | Miyano |
| 6,852,097 B1 | 2/2005 | Fulton, III |
| 6,858,019 B2 | 2/2005 | McGuckin, Jr. et al. |
| 6,872,198 B1 | 3/2005 | Wilson et al. |
| 6,878,143 B2 | 4/2005 | Andersen |
| 6,881,211 B2 | 4/2005 | Schweikert et al. |
| 6,884,253 B1 | 4/2005 | McFarlane |
| 6,911,014 B2 | 6/2005 | Wentling et al. |

(56) References Cited

U.S. PATENT DOCUMENTS

| | | |
|---|---|---|
| 6,913,601 B2 | 7/2005 | St. Goar et al. |
| 6,916,313 B2 | 7/2005 | Cunningham |
| 6,921,396 B1 | 7/2005 | Wilson et al. |
| 6,921,411 B2 | 7/2005 | Yock |
| 6,934,142 B2 | 8/2005 | Grosse et al. |
| 6,966,886 B2 | 11/2005 | Appling |
| 6,969,381 B2 | 11/2005 | Voorhees |
| 6,979,318 B1 | 12/2005 | McDonald et al. |
| 6,991,625 B1 | 1/2006 | Gately et al. |
| D515,211 S | 2/2006 | Chesnin |
| 6,997,894 B2 | 2/2006 | Caresio |
| 7,008,395 B1 | 3/2006 | Loggie |
| 7,011,645 B2 | 3/2006 | McGuckin, Jr. et al. |
| 7,018,384 B2 | 3/2006 | Skakoon |
| 7,029,467 B2 | 4/2006 | Currier et al. |
| 7,066,914 B2 | 6/2006 | Andersen |
| 7,066,925 B2 | 6/2006 | Gately et al. |
| 7,074,213 B2 | 7/2006 | McGuckin, Jr. et al. |
| 7,077,829 B2 | 7/2006 | McGuckin, Jr. et al. |
| 7,087,053 B2 | 8/2006 | Vanney |
| 7,090,654 B2 | 8/2006 | Lotito et al. |
| 7,108,674 B2 | 9/2006 | Quinn |
| D530,420 S | 10/2006 | Chesnin |
| 7,128,734 B1 | 10/2006 | Wilson et al. |
| 7,130,700 B2 | 10/2006 | Gardeski et al. |
| 7,141,035 B2 | 11/2006 | Haggstrom |
| RE39,451 E | 12/2006 | Kuhle |
| 7,182,746 B2 | 2/2007 | Haarala et al. |
| 7,300,430 B2 | 11/2007 | Wilson et al. |
| 7,322,953 B2 | 1/2008 | Redinger |
| 7,347,852 B2 | 3/2008 | Hobbs et al. |
| 7,381,204 B2 | 6/2008 | Wilson et al. |
| 7,393,339 B2 | 7/2008 | Zawacki et al. |
| 7,422,571 B2 | 9/2008 | Schweikert et al. |
| 7,465,286 B2 | 12/2008 | Patterson et al. |
| 7,485,107 B2 | 2/2009 | DiFiore et al. |
| 7,569,029 B2 | 8/2009 | Clark |
| 7,575,563 B2 | 8/2009 | Appling |
| 7,651,482 B2 | 1/2010 | Harris |
| 7,686,823 B2 | 3/2010 | Pingleton et al. |
| 7,798,999 B2 | 9/2010 | Bailey et al. |
| 7,972,465 B2 | 7/2011 | Patterson et al. |
| 8,021,321 B2 | 9/2011 | Zawacki |
| 8,066,660 B2 | 11/2011 | Gregersen et al. |
| 8,092,415 B2 | 1/2012 | Moehle |
| 8,100,863 B2 | 1/2012 | Moehle et al. |
| 8,152,951 B2 | 4/2012 | Zawacki et al. |
| 8,206,371 B2 | 6/2012 | Nimkar et al. |
| 8,292,841 B2 | 10/2012 | Gregersen |
| 8,500,939 B2 | 8/2013 | Nimkar et al. |
| 8,540,661 B2 | 9/2013 | Gregersen |
| 8,597,275 B2 | 12/2013 | Nimkar et al. |
| 8,696,614 B2 | 4/2014 | Gregersen et al. |
| 8,808,227 B2 | 8/2014 | Zawacki et al. |
| 8,894,601 B2 | 11/2014 | Moehle et al. |
| 8,992,454 B2 | 3/2015 | Anand |
| 2001/0041857 A1 | 11/2001 | Sansoucy |
| 2001/0041873 A1 | 11/2001 | Dopper et al. |
| 2002/0013569 A1 | 1/2002 | Sterman et al. |
| 2002/0026156 A1 | 2/2002 | Quinn |
| 2002/0055724 A1 | 5/2002 | Hughes |
| 2002/0086047 A1 | 7/2002 | Mueller et al. |
| 2002/0087108 A1 | 7/2002 | Maginot et al. |
| 2002/0087145 A1 | 7/2002 | Ehwald et al. |
| 2002/0091362 A1 | 7/2002 | Maginot et al. |
| 2002/0091430 A1 | 7/2002 | Dobak et al. |
| 2002/0099326 A1 | 7/2002 | Wilson et al. |
| 2002/0099327 A1 | 7/2002 | Wilson et al. |
| 2002/0107506 A1 | 8/2002 | McGuckin et al. |
| 2002/0138031 A1 | 9/2002 | Ross |
| 2002/0169490 A1 | 11/2002 | Noda et al. |
| 2002/0173770 A1 | 11/2002 | Flory et al. |
| 2002/0177904 A1 | 11/2002 | Huxel et al. |
| 2003/0023198 A1 | 1/2003 | Twardowski |
| 2003/0088213 A1 | 5/2003 | Schweikert et al. |
| 2003/0093027 A1 | 5/2003 | McGuckin et al. |
| 2003/0097091 A1 | 5/2003 | Hobbs et al. |
| 2003/0144623 A1 | 7/2003 | Heath et al. |
| 2003/0149395 A1 | 8/2003 | Zawacki |
| 2003/0153898 A1 | 8/2003 | Schon et al. |
| 2003/0187411 A1 | 10/2003 | Constantz |
| 2003/0204179 A1 | 10/2003 | Davey et al. |
| 2004/0039350 A1 | 2/2004 | McKittrick |
| 2004/0054321 A1 | 3/2004 | Schon et al. |
| 2004/0059314 A1 | 3/2004 | Schon et al. |
| 2004/0064086 A1 | 4/2004 | Gottlieb et al. |
| 2004/0065333 A1 | 4/2004 | Wilson et al. |
| 2004/0075198 A1 | 4/2004 | Schweikert et al. |
| 2004/0087892 A1 | 5/2004 | Cunningham |
| 2004/0092863 A1 | 5/2004 | Raulerson et al. |
| 2004/0097863 A1 | 5/2004 | Appling |
| 2004/0097903 A1 | 5/2004 | Raulerson |
| 2004/0122418 A1 | 6/2004 | Voorhees |
| 2004/0147903 A1 | 7/2004 | Latini |
| 2004/0167463 A1 | 8/2004 | Zawacki et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0193102 A1 | 9/2004 | Haggstrom |
| 2004/0210180 A1 | 10/2004 | Altman |
| 2004/0210187 A1 | 10/2004 | Zawacki |
| 2004/0210237 A1 | 10/2004 | Ross et al. |
| 2004/0220550 A1 | 11/2004 | Schryver |
| 2004/0230204 A1 | 11/2004 | Wortley et al. |
| 2004/0243095 A1 | 12/2004 | Nimkar et al. |
| 2004/0249337 A1 | 12/2004 | DiFiore |
| 2005/0003322 A1 | 1/2005 | Logan et al. |
| 2005/0004504 A1 | 1/2005 | Frye et al. |
| 2005/0013341 A1 | 1/2005 | Baghai |
| 2005/0025641 A1 | 2/2005 | Shibata et al. |
| 2005/0027282 A1 | 2/2005 | Schweikert et al. |
| 2005/0027289 A1 | 2/2005 | Castellano et al. |
| 2005/0033222 A1 | 2/2005 | Haggstrom et al. |
| 2005/0033264 A1 | 2/2005 | Redinger |
| 2005/0054989 A1 | 3/2005 | McGuckin et al. |
| 2005/0055012 A1 | 3/2005 | Trerotola |
| 2005/0059925 A1 | 3/2005 | Maginot et al. |
| 2005/0070842 A1 | 3/2005 | Lotito et al. |
| 2005/0080398 A1 | 4/2005 | Markel et al. |
| 2005/0085765 A1 | 4/2005 | Voorhees |
| 2005/0096585 A1 | 5/2005 | Schon et al. |
| 2005/0113904 A1 | 5/2005 | Shank et al. |
| 2005/0131341 A1 | 6/2005 | McGuckin et al. |
| 2005/0171469 A1 | 8/2005 | Cunningham |
| 2005/0187535 A1 | 8/2005 | Wilson et al. |
| 2005/0209582 A1 | 9/2005 | Quinn et al. |
| 2005/0215977 A1 | 9/2005 | Uschold |
| 2005/0228339 A1 | 10/2005 | Clark |
| 2005/0245900 A1 | 11/2005 | Ash |
| 2005/0251190 A1 | 11/2005 | McFarlane |
| 2005/0256461 A1 | 11/2005 | DiFiore et al. |
| 2005/0261663 A1 | 11/2005 | Patterson et al. |
| 2005/0267400 A1 | 12/2005 | Haarala et al. |
| 2005/0277862 A1 | 12/2005 | Anand |
| 2005/0283111 A1 | 12/2005 | Maurice |
| 2005/0288623 A1 | 12/2005 | Hjalmarsson |
| 2005/0288706 A1 | 12/2005 | Widomski et al. |
| 2006/0004316 A1 | 1/2006 | Difiore et al. |
| 2006/0004325 A1 | 1/2006 | Hamatake et al. |
| 2006/0009783 A1 | 1/2006 | Rome et al. |
| 2006/0015072 A1 | 1/2006 | Raulerson |
| 2006/0015130 A1 | 1/2006 | Voorhees et al. |
| 2006/0030827 A1 | 2/2006 | Raulerson et al. |
| 2006/0047267 A1 | 3/2006 | Gately et al. |
| 2006/0047268 A1 | 3/2006 | Stephens |
| 2006/0058775 A1 | 3/2006 | Stevens et al. |
| 2006/0064072 A1 | 3/2006 | Gately et al. |
| 2006/0095062 A1 | 5/2006 | Stephens |
| 2006/0100572 A1 | 5/2006 | DiMatteo et al. |
| 2006/0161100 A1 | 7/2006 | Hamboly |
| 2006/0184142 A1 | 8/2006 | Schon et al. |
| 2006/0189922 A1 | 8/2006 | Amarasinghe et al. |
| 2006/0200111 A1 | 9/2006 | Moehle et al. |
| 2006/0206094 A1 | 9/2006 | Chesnin et al. |

(56) References Cited

U.S. PATENT DOCUMENTS

| | | |
|---|---|---|
| 2006/0251612 A1 | 11/2006 | Kotzev et al. |
| 2006/0253063 A1 | 11/2006 | Schweikert |
| 2006/0271012 A1 | 11/2006 | Canaud et al. |
| 2007/0005003 A1 | 1/2007 | Patterson et al. |
| 2007/0019181 A1 | 1/2007 | Sinclair et al. |
| 2007/0066964 A1 | 3/2007 | Atkins |
| 2007/0078478 A1 | 4/2007 | Atkins et al. |
| 2007/0106206 A1 | 5/2007 | Appling |
| 2007/0129704 A1 | 6/2007 | O'Mahony et al. |
| 2007/0167925 A1 | 7/2007 | Jacqmein |
| 2007/0191810 A1 | 8/2007 | Kennedy |
| 2007/0225661 A1 | 9/2007 | Ash et al. |
| 2007/0225682 A1 | 9/2007 | Ash et al. |
| 2007/0282274 A1 | 12/2007 | Chesnin |
| 2008/0021417 A1 | 1/2008 | Zawacki et al. |
| 2008/0039774 A1 | 2/2008 | Zawacki et al. |
| 2008/0065029 A1 | 3/2008 | Racz |
| 2008/0082079 A1 | 4/2008 | Braga et al. |
| 2008/0082080 A1 | 4/2008 | Braga |
| 2008/0097409 A1 | 4/2008 | Stephens |
| 2008/0172012 A1 | 7/2008 | Hiniduma-Lokuge et al. |
| 2008/0214980 A1 | 9/2008 | Anand |
| 2008/0214992 A1 | 9/2008 | Haarala et al. |
| 2009/0112153 A1 | 4/2009 | Gregersen et al. |
| 2009/0118661 A1 | 5/2009 | Moehle et al. |
| 2009/0118701 A1 | 5/2009 | Nimkar et al. |
| 2009/0118707 A1 | 5/2009 | Schweikert et al. |
| 2009/0118755 A1 | 5/2009 | Maliglowka et al. |
| 2009/0138034 A1 | 5/2009 | Maliglowka et al. |
| 2009/0157051 A1 | 6/2009 | Appling et al. |
| 2009/0187141 A1 | 7/2009 | Lareau et al. |
| 2009/0192435 A1 | 7/2009 | Gregersen |
| 2009/0204052 A1 | 8/2009 | Nimkar et al. |
| 2009/0204079 A1 | 8/2009 | Nimkar et al. |
| 2009/0204083 A1 | 8/2009 | O'Donnell et al. |
| 2009/0205189 A1 | 8/2009 | Nimkar et al. |
| 2009/0209940 A1 | 8/2009 | Nimkar et al. |
| 2009/0292248 A1 | 11/2009 | Schon et al. |
| 2009/0312687 A1 | 12/2009 | DeFonzo et al. |
| 2010/0081986 A1 | 4/2010 | Matson et al. |
| 2010/0331780 A1 | 12/2010 | Bellisario et al. |
| 2011/0020418 A1 | 1/2011 | Bosley, Jr. et al. |
| 2012/0059304 A1 | 3/2012 | Gregersen et al. |
| 2012/0089070 A1 | 4/2012 | Moehle et al. |
| 2013/0018405 A1 | 1/2013 | Onishi et al. |
| 2013/0079752 A1 | 3/2013 | Gregersen |
| 2013/0253445 A1 | 9/2013 | Nimkar et al. |
| 2014/0018772 A1 | 1/2014 | Ash |
| 2014/0025042 A1 | 1/2014 | Gregersen |
| 2014/0228742 A1 | 8/2014 | Gregersen et al. |
| 2014/0276472 A1 | 9/2014 | VanderStek et al. |
| 2014/0276493 A1 | 9/2014 | Leung et al. |
| 2014/0277052 A1 | 9/2014 | Haselby et al. |
| 2014/0330220 A1 | 11/2014 | Zawacki et al. |
| 2014/0336687 A1 | 11/2014 | Iwase et al. |
| 2015/0073336 A1 | 3/2015 | Moehle et al. |
| 2015/0088100 A1 | 3/2015 | Oborn et al. |
| 2015/0335810 A1 | 11/2015 | Anand |

FOREIGN PATENT DOCUMENTS

| | | |
|---|---|---|
| CA | 2474351 A1 | 8/2003 |
| CN | 2788836 Y | 6/2006 |
| CN | 101918067 A | 12/2010 |
| CN | 103170050 A | 6/2013 |
| CN | 101918066 B | 7/2013 |
| DE | 8815869 U1 | 2/1989 |
| DE | 9108132 U1 | 9/1991 |
| DE | 102005051211 A1 | 5/2007 |
| EP | 0030854 A2 | 6/1981 |
| EP | 0132344 A2 | 1/1985 |
| EP | 0301854 | 2/1989 |
| EP | 0332366 A2 | 9/1989 |
| EP | 0386408 A1 | 9/1990 |
| EP | 0453234 A1 | 10/1991 |
| EP | 0476796 A1 | 3/1992 |
| EP | 0495263 A1 | 7/1992 |
| EP | 0650740 A1 | 5/1995 |
| EP | 0711574 A1 | 5/1996 |
| EP | 1471966 A1 | 11/2004 |
| EP | 1599247 A2 | 11/2005 |
| GB | 1503469 | 3/1978 |
| JP | 56-136569 A | 10/1981 |
| JP | 8-510935 T | 11/1996 |
| JP | 2001137350 | 5/2001 |
| JP | 2008500081 A | 1/2008 |
| JP | 4827377 B2 | 11/2011 |
| MX | 249060 | 9/2007 |
| RU | 45923 A | 11/2004 |
| SU | 459237 A1 | 2/1975 |
| WO | 9108132 A1 | 6/1991 |
| WO | 9316741 A1 | 9/1993 |
| WO | 9316752 A1 | 9/1993 |
| WO | 9709086 A1 | 3/1997 |
| WO | 9717102 | 5/1997 |
| WO | 9722374 A1 | 6/1997 |
| WO | 9737699 | 10/1997 |
| WO | 9904844 A1 | 2/1999 |
| WO | 0023137 A1 | 4/2000 |
| WO | 2002018004 A2 | 3/2002 |
| WO | 02058776 A2 | 8/2002 |
| WO | 02083223 A1 | 10/2002 |
| WO | 03030960 A2 | 4/2003 |
| WO | 03033049 A2 | 4/2003 |
| WO | 03066148 A1 | 8/2003 |
| WO | 2004075962 A2 | 9/2004 |
| WO | 2004096334 | 11/2004 |
| WO | 2004112876 | 12/2004 |
| WO | 2005018712 A2 | 3/2005 |
| WO | 2005023336 A2 | 3/2005 |
| WO | 2005077449 | 8/2005 |
| WO | 2005084741 A1 | 9/2005 |
| WO | 2005118039 A1 | 12/2005 |
| WO | 2006034877 | 4/2006 |
| WO | 2009051967 A1 | 4/2009 |
| WO | 2009055332 A1 | 4/2009 |
| WO | 2009059220 A1 | 5/2009 |
| WO | 2015077560 A1 | 5/2015 |
| WO | 2016/011091 A1 | 1/2016 |

OTHER PUBLICATIONS

Hull, et al., The Groshong Catheter: Initial Experience and Early Results of Imaging-guided Placement1, Radiology, 1992, vol. 185, pp. 803-807.

Ignotus, et al., Review of Radiological Insertion of Indwelling Central Venous Catheters, Minimally Invasive Therapy, 1992, 1:373-388.

Instructions for Use (Copyright Dated 1990) for Polycath Polyurethance Central Venous Catheter; believed to have been packaged with product and sold in the United States before Jan. 4, 2000 and with related marketing materials.

Instructions for Use (Copyright Dated 1992) for FloLock Single Lumen Bi-directional Valved Catheter; believed to have been packaged with product and sold in the United States before Jan. 2000.

Instructions for Use (not dated) for Infuse-a-Cath Polyurethance Central Venous Catheter; believed to have been packaged with product and sold in the United States before Jan. 2000.

Instructions for Use for Diatek Cannon Catheter Product First Sold in the United States in Sep. 2001.

Jones, et al., Efficacy of the Supraclavicular Route for Temporary Hemodialysis Access, Southern Medical Journal, 1992, vol. 85, No. 7, pp. 725-726.

JP 2010-532299 filed Apr. 30, 2010 Final Notice of Reason for Rejection dated Feb. 8, 2013.

JP 2010-532299 filed Apr. 30, 2010 Official Action dated Apr. 23, 2012.

JP App. No. 2003-565569 filed Feb. 7, 2003, Translated Decision of Refusal mailed Dec. 24, 2009.

JP App. No. 2003-565569 filed Feb. 7, 2003, Translated Official Action mailed May 28, 2009.

(56) References Cited

OTHER PUBLICATIONS

JP App. No. 2003-565569 filed Feb. 7, 2003, Translated Official Action mailed Nov. 7, 2008.
Kapoian et al. Dialysis as Treatment of End-Stage Renal Disease, Chapter 5: Dialysis Access and Recirculation, © 1999.
Kaupke, et al., Perforation of the Superior Vena Cava by a Subclavian Hemodialysis Catheter: early detection by angiography, The International Journal of Artificial Organs, 1992, vol. 15, No. 11, pp. 666-668.
Kelber, et al., Factors Affecting Delivery of High-Efficiency Dialysis Using Temporary Vascular Access, American Journal of Kidney Diseases, 1993, vol. 22, No. 1, pp. 24-29.
Lumsden, et al., Hemodialysis Access in the Pediatric Patient Population, The American Journal of Surgery, 1994, vol. 168, pp. 197.
Lund, "Percutaneous Translumbar Inferior Vena Cava Cannulation and other Alternative Vascular Access Techniques" in Venous Interventional Radiology with Clinical Perspectives, Savader et al, eds. pp. 251-61, Apr. 10, 2000.
Lund, et al., Percutaneous Translumbar Inferior Vena Cava Cannulation for Hemodialysis, American Journal of Kidney Diseases, 1995, vol. 25, No. 5, pp. 732-737.
Maki, D., Pathogenesis, Prevention, and Management of Infections Due to Intravascular Devices Used for Infusion Therapy, in Infections Associated with Indwelling Medical Devices, Bisno et al, eds, American Society for Microbiology, 1989, pp. 161-177.
Malviya et al., "Vascular Access in Gynecological Cancer Using the Groshong Right Atrial Catheter", Gynecological Oncology 33, 313-316 (1989).
Mauro, et al., Radiologic Placement of Long-term Central Venous Catheters: A Review, JVIR, 1993, vol. 4, No. 1, pp. 127-137.
McGee, et al., Accurate placement of central venous catheters: A prospective, randomized, multicenter trial, Critical Care Medicine, 1993, vol. 21, No. 8, pp. 1118-1123.
Medcomp, For Access via the Internal Jugular Vein . . . The Medcomp TESIO Catheter is the Solution: The Short and Long Term Solution to Subclavian Venin Stenosis and Difficult Access Problems, Brochure, 4 pages, 1991.
Medcomp® Brochure , "Ash Split Cath™ XL", Dec. 2001, PN 2291.
Medcomp® Brochure , "Ash Split Cath™", Guidewire Weave Insertion Technique, Jan. 2002, PN 2296.
Medcomp® Brochure , "Ash Split Cath™", Jul. 2001, PN 2114.
Medcomp® Brochure , "Ash Split Cath™", Nov. 1997, PN 2050.
Medcomp® Brochure , "Ash Split Cath® II", Aug. 2002, PN 2334.
Medcomp® Brochure , "Magna™ High Flow Catheter", Mar. 2002, PN 2321.
Moss et al, Use of Silicone Dual-Lumen Catheter with a Dacron Cuff as a Long Term Vascular Access for Hemodialysis Patients, Amer J Kidney Diseases, vol. XVI, No. 3, pp. 211-215, Sep. 1990.
Moss, et al., Use of a Silicone Catheter With a Dacron Cuff for Dialysis Short-Term Vascular Access, American Journal of Kidney Diseases, 1988, vol. XII, No. 6, pp. 492-498.
Myers, R.D. et al, New Double-lumen Polyethylene Cannula for Push-pull Perfusion of Brain Tissue in Vivo, Journal of Neuroscience Methods, pp. 205-218, vol. 12, 1985.
Northsea, C., Using Urokinase to Restore Patency in Double Lumen Catheters, ANNA Journal 1994, vol. 21, No. 5, pp. 261-273.
OriGen, OriGen Biomedical Dual Lumen Catheter, from <http://origen.net/catheter.html>, downloaded May 13, 2009, 4 pages (reprinted for submission on Jul. 21, 2011).
Parsa, et al., Establishment of Intravenous Lines for Long-term Intravenous Therapy and Monitoring, Surgical Clinics of N. Am. 1985, vol. 65, No. 4, pp. 835-865.
Parsa, et al., Vascular Access Techniques, Textbook of Critical Care, W.B. Saunders, Philadelphia, PA (1989), pp. 122-127.
Pasquale, et al., Groshong® Versus Hickman® Catheters, SURGERY, Gynecology & Obstetrics, 1992, vol. 174, pp. 408-410.
Passaro, et al., Long-term Silastic Catheters and Chest Pain, Journal of Parenteral and Enteral Nutrition, 1994, vol. 18, No. 3, pp. 240-242.
Patel et al., "Sheathless Technique of Ash Split-Cath Insertion", 12 JVIR 376-78 (Mar. 2001).
Paulsen, et al., Use of Tissue Plasminogen Activator for Reopening of Clotted Dialysis Catheters, Nephron, 1993, vol. 64, pp. 468-470.
PCT/US2003/003751 filed Feb. 7, 2003 Preliminary Examination Report dated May 5, 2004.
PCT/US2003/003751 filed Feb. 7, 2003 Search Report dated Jul. 3, 2003.
PCT/US2004/005102 filed Feb. 19, 2004 Preliminary Report Patentability dated Aug. 29, 2005.
PCT/US2004/005102 filed Feb. 19, 2004 Search Report dated Dec. 27, 2004.
PCT/US2004/005102 filed Feb. 19, 2004 Written Opinion dated Aug. 21, 2005.
PCT/US2008/078551 filed Oct. 2, 2008 International Preliminary Report on Patentability dated Apr. 20, 2010.
PCT/US2008/078551 filed Oct. 2, 2008 Search Report dated Mar. 13, 2009.
PCT/US2008/078551 filed Oct. 2, 2008 Written Opinion dated Mar. 13, 2009.
PCT/US2008/078560 filed Oct. 2, 2008 Preliminary Report on Patentability dated Aug. 26, 2010.
PCT/US2008/078560 filed Oct. 2, 2008 Search Report dated Mar. 16, 2009.
PCT/US2008/078560 filed Oct. 2, 2008 Written Opinion dated Mar. 16, 2009.
PCT/US2008/078566 filed Oct. 2, 2008 International Preliminary Report on Patentability dated Apr. 20, 2010.
PCT/US2008/078566 filed Oct. 2, 2008 Search Report dated Mar. 19, 2009.
PCT/US2008/078566 filed Oct. 2, 2008 Written Opinion dated Mar. 19, 2009.
PCT/US2008/078571 filed Oct. 2, 2008 Preliminary Report on Patentability dated Aug. 26, 2010.
PCT/US2008/078571 filed Oct. 2, 2008 Search Report dated Mar. 20, 2009.
PCT/US2008/078571 filed Oct. 2, 2008 Written Opinion dated Mar. 20, 2009.
PCT/US2008/080463 filed 10/20/08 Preliminary Report on Patentability dated 04/27/10.
PCT/US2008/080463 filed 10/20/08 Search Report dated 03/16/09.
PCT/US2008/080463 filed 10/20/08 Written Opinion dated 04/16/09.
PCT/US2008/082106 filed 10/31/08 International Preliminary Report on Patentability dated 5/4/10.
PCT/US2008/082106 filed 10/31/08 Search Report dated 01/12/09.
PCT/US2008/082106 filed 10/31/08 Written Opinion dated 01/12109.
Picture of Device believed to be partial sample of a product believed to have been sold in the United States with Polycath and/or Infuse-a-Cath Instructions for Use, 1 page, 2011.
Quinton® Catheter Products (1993).
Raaf Dual Lumen Right Atrial Catheters Brochure—Quinton Instrument Co., 6 pages, 1993.
Raaf, et al., Open Insertion of Right Atrial Catheters Through the Jugular Veins, SURGERY, Gynecology & Obstetrics, 1993, vol. 177, pp. 295-298.
Rawn, et al., The Hemodialysis Access, Chapter 9, pp. 9.1-9.11, available at <<http://msl1.mit.edu/ESD10/kidneys/HndbkPDF/Chap09.pdf>>, last accessed Jun. 4, 2012.
Schwab, et al., Prospective Evaluation of a Dacron Cuffed Hemodialysis Catheter for Prolonged Use, American Journal of Kidney Diseases, 1988, vol. XI, No. 2, pp. 166-169.
Schwab, et al., Vascular Access: Case Oriented Discussions of Selected Critical Issues: Hemodialysis Catheters for Permanent Use, 1999.
Septum, Wikipedia, The Free Encyclopedia, hhtp://en.wikipedia.org/wiki/Septum (last visited Dec. 18, 2012) (defining "septum" as "a wall, dividing a cavity or structure into smaller ones").

(56) References Cited

OTHER PUBLICATIONS

Shaffer, D., Catheter-Related Sepsis Complicating Long-Term Tunnelled Central Venous Dialysis Catheters: Management by Guidewire Exchange, American Journal of Kidney Diseases, 1995, vol. 25, No. 4, pp. 593-596.
Shaffer, D., Lessons From Vascular Access Procedures for Hemodialysis, Surgical Oncology Clinics of North America, 1995, vol. 4, No. 3, pp. 537-549.
Sioshansi, P., New Processes for Surface Treatment of Catheters, Artificial Organs, 1994, 18(4):266-271.
Swartz, et al., Successful Use of Cuffed Centrol Venous Hemodialysis Catheters Inserted Percutaneously, J. Am. Soc. Nephrol., 1994, 4:1719-1725.
Taber's Cyclopedic Medical Dictionary 1662 (16th ed. 1989) (defining "septum" as a "wall dividing two cavities").
Tal, Michael G, Comparison of Recirculation Percentage of the Palindrome Catheter and Standard Hemodialysis Catheters in a Swine Model, J Vasc Interv Radiol, pp. 1237-1240, vol. 16, No. 9, 2005.
Tesio, et al., Double Catheterization of the Internal Jugular Vein for Hemodialysis: Indications, Techniques, and Clinical Results, Artificial Organs, 1994, vol. 18, No. 4, pp. 301-304.
The Groshong™ Peripherally Inserted Central Venous Catheter Brochure—Cath-tech®, 4 pages, 1988.
Transcript of Videotaped Deposition of Gregory Haas (Excerpt), Sep. 23, 2003, *Thierry Pourchez and Bard Access Systems, Inc.* v. *Diatek, Inc. and Arrow International, Inc.*, Civil Action No. 03-CV-0972 (S.D.N.Y.).
Transcript of Videotaped Deposition of Thierry Pourchez, vol. 1, Oct. 16, 2003, *Thierry Pourchez and Bard Access Systems, Inc.* v. *Diatek, Inc. and Arrow International, Inc.*, Civil Action No. 03-CV-0972 (S.D.N.Y.).
Transcript of Videotaped Deposition of Thierry Pourchez, vol. 2, Oct. 17, 2003, *Thierry Pourchez and Bard Access Systems, Inc.* v. *Diatek, Inc. and Arrow International, Inc.*, Civil Action No. 03-CV-0972 (S.D.N.Y.).
Treiman, et al., Chronic Venous Access in Patients with Cancer, CANCER, 1993, vol. 72, No. 3, pp. 760-765.
Twardowski et al. "Side Holes at the Tip of Chronic Hemodialysis Catehters are Harmful," The Journal of Vascular Access 2001; 2:8-16.
Twardowski et al., "Blood Recirculation in Intravenous Catheters for Hemodialysis" J. Am. Soc. Nephrol. 3:1978-81 (1993).
TYCO Healthcare, MAHURKAR Dual Lumen Catheters, Informational Brochure, 2 pages, 2004.
TYCO Healthcare, MAHURKAR QPlus High Flow Acute Care Catheter, Informational Brochure, 2 pages, 2004.
TYCO Healthcare, Tal Palindrome™ Dual Lumen Catheters Order Information, Features and Benefits, Frequently Asked Questions, printed from http://www.kendallvasculartherapy.com/VascularTherapy, 6 pages, on Mar. 1, 2007.
Uldall, P., Subclavian Cannulation is No Longer Necessary or Justified in Patients with End-Stage Renal Failure, Seminars in Dialysis, 1994, vol. 7, No. 3, pp. 161-164.
U.S. Appl. No. 10/371,774, filed Feb. 21, 2003 Final Office Action dated Jan. 19, 2007.
U.S. Appl. No. 10/371,774, filed Feb. 21, 2003 Final Office Action dated Mar. 7, 2007.
U.S. Appl. No. 10/371,774, filed Feb. 21, 2003 Non-Final Office Action dated Jul. 17, 2006.
U.S. Appl. No. 10/371,774, filed Feb. 21, 2003 Notice of Allowance dated Jun. 1, 2007.
U.S. Appl. No. 10/445,731, filed May 27, 2003 Non-Final Office Action dated Apr. 13, 2007.
U.S. Appl. No. 10/445,731, filed May 27, 2003 Non-Final Office Action dated Dec. 12, 2008.
U.S. Appl. No. 10/445,731, filed May 27, 2003 Non-Final Office Action dated May 30, 2008.
U.S. Appl. No. 10/842,586, filed May 10, 2004 Advisory Action dated Oct. 9, 2008.
U.S. Appl. No. 10/842,586, filed May 10, 2004 Final Office Action dated Jul. 29, 2008.
U.S. Appl. No. 10/842,586, filed May 10, 2004 Final Office Action dated May 25, 2010.
U.S. Appl. No. 12/414,467, filed Mar. 30, 2009 Notice of Allowance dated May 31, 2012.
U.S. Appl. No. 12/414,467, filed Mar. 30, 2009 Non-Final Office Action dated Aug. 11, 2011.
U.S. Appl. No. 13/294,941, filed Nov. 11, 2011 Non-Final Office Action dated May 31, 2013.
U.S. Appl. No. 13/445,713, filed Apr. 12, 2012 Advisory Action dated Aug. 8, 2013.
U.S. Appl. No. 13/445,713, filed Apr. 12, 2012 Final Office Action dated May 30, 2013.
U.S. Appl. No. 13/445,713, filed Apr. 12, 2012 Non-Final Office Action dated Jan. 2, 2013.
U.S. Appl. No. 13/445,713, filed Apr. 12, 2012 Notice of Allowance dated Oct. 18, 2013.
US Patent File History U.S. Pat. No. 5,403,291 (Abrahamson).
US Patent File History U.S. Pat. No. 5,489,278 (Abrahamson).
US Patent File History U.S. Pat. No. 5,685,867 (Twardowski et al.).
Wechsler, et al., Thrombosis and Infection Caused by Thoracic Venous Catheters: Pathogenesis and Imagings Findings, AJR, 1993; 160:467-471.
Weitzel, et al., Successful Use of Indwelling Cuffed Femoral Vein Catheters in Ambulatory Hemodialysis Patients, American Journal of Kidney Diseases, 1993, vol. 22, No. 3, pp. 426-429.
Arrow Cannon II Plus Brochure, 2006.
*Arrow International, Inc. et al* v. *Spire Biomedical, Inc.*, U.S. Dist Ct Dist MA CA No. 06-CV-11564-DPW, Declaration of Dr. Karim Valji (Jul. 17, 2008).
*Arrow International, Inc. et al* v. *Spire Biomedical, Inc.*, U.S. Dist Ct Dist MA CA No. 06-CV-11564-DPW, Declaration of Kenneth Todd Cassidy (Jul. 16, 2008).
*Arrow International, Inc. et al* v. *Spire Biomedical, Inc.*, U.S. Dist Ct Dist MA CA No. 06-CV-11564-DPW, Declaration of Rebecca R. Eisenberg in Opposition to Defendant's Motion for Partial Summary Judgment of Invalidity (Jun. 8, 2009).
*Arrow International, Inc. et al* v. *Spire Biomedical, Inc.*, U.S. Dist Ct Dist MA CA No. 06-CV-11564-DPW, Memorandum of Law in Support of Defendant's Motion for Summary Judgment on Invalidity [Redacted Pursuant to Jun. 10, 2008 Order on Motion to Seal].
*Arrow International, Inc. et al* v. *Spire Biomedical, Inc.*, U.S. Dist Ct Dist MA CA No. 06-CV-11564-DPW, Memorandum of Law in Support of Defendant's Motion for Summary Judgment on Invalidity Exhibit A (Jul. 10, 2009).
*Arrow International, Inc. et al* v. *Spire Biomedical, Inc.*, U.S. Dist Ct Dist MA CA No. 06-CV-11564-DPW, Plaintiff's Memorandum in Opposition to Defendant's Motion for Summary Judgement on Non-Infringement (Jul. 17, 2008).
*Arrow International, Inc. et al* v. *Spire Biomedical, Inc.*, U.S. Dist. Ct. Dist. MA CA No. 06-CV-11564-DPW, Defendant's Omnibus Statement of Material Facts in Support of its Motions for Summary Judgment (Jun. 10, 2008) [Redacted Pursuant to Jun. 10, 2008 Order on Motion to Seal].
Bander, et al., Central Venous Angioaccess for Hemodialysis and Its Complications, Seminars in Dialysis, 1992, vol. 5, No. 2, pp. 121-128.
Baranowski, L., Central Venous Access Devices, Journal of Intravenous Nursing, 1993, vol. 16, No. 3, pp. 167-194.
Bard Access Systems Hickman® , Leonard® , and Broviac® Central Venous Catheters (Long Term), Instructions for Use, 31 pages, 1999.
Bard Access Systems Hickman® , Leonard® , and Broviac® Central Venous Catheters, Nursing Procedural Manual, 52 pages, Jun. 1994.
Bard Davol® Hickman® Round Dual Lumen Catheters for Central Venous Access Informational Brochure, 4 pages, 1994.
Bard Hickman® Catheters Informational Brochure, 3 pages, 1994.
Believed to be an unpublished sketch of a conception by Dr. John Frusha; date of sketch believed to be Jun. 24, 1997.
Berkoben, et al., Maintenance of Permanent Hemodialysis Vascular Access Patency, ANNA Journal, 1995, vol. 22, No. 1, pp. 17-24.

(56) References Cited

OTHER PUBLICATIONS

Bolz, et al., Catheter Malfunction and Thrombus Formation on Double-Lumen Hemodialysis Catheters: An Intravascular Ultrasonographic Study, American Journal of Kidney Diseases, 1995, vol. 25, No. 4, pp. 597-602.
Bour, et al., Experience With the Double Lumen Silastic® Catheter for Hemoaccess, Surgery, Gynecology & Obstetrics, 1990, vol. 171, pp. 33-39.
Camp, "Care of the Groshong Catheter", Oncol Nurs Forum, vol. 15, No. 6, 1988.
Campbell, et al., Radiological Insertion of Long-term Venous Access Devices, Seminars in Interventional Radiology, 1994, vol. II, No. 4, pp. 366-375.
Canaud, B et al, Permenant Twin Catheter: A Vascular Access Option of Choice for Haemodialysis in Elderly Patients, pp. 82-88, vol. 17 No. 7, 1994.
Claim Construction Order of Federal District Court dated May 9, 2003 in *Thierry Pourchez and Bard Access Systems, Inc. v. Diatek, Inc. and Arrow International, Inc.* litigation (S.D. N.Y. 03 Civ. 0972).
Claim Construction Order of Federal District Court dated Oct. 31, 2006 in *Arrow Int'l. Inc.and Arrow Int'l. Investment Corp. v. Spire Biomedical, Inc.* litigation (D. Mass. Civil Action No. 06-CV-11564).
CN 200880121182.0 filed Oct. 20, 2008 First Office Action dated May 2, 2012.
CN 200880121183.5 filed Oct. 2, 2008 First Office Action dated Mar. 28, 2012.
CN 200880121183.5 filed Oct. 2, 2008 Second Office Action dated Aug. 17, 2012.
CN 200880121183.5 filed Oct. 2, 2008 Third Office Action dated Dec. 11, 2012.
CN 200880123095.9 filed Oct. 20, 2008 First Office Action dated Feb. 13, 2012.
CN 200880123095.9 filed Oct. 20, 2008 Second Office Action dated Dec. 18, 2012.
CN 200880123533.1 filed Jun. 30, 2008 First Office Action dated May 28, 2012.
CN 200880123533.1 filed Jun. 30, 2008 Notice of Grant dated Dec. 24, 2012.
Decision of Federal District Court dated Jul. 7, 2009 granting Summary Judgement of Invalidity in *Arrow Int'l. Inc.and Arrow Int'l Investment Corp. v. Spire Biomedical, Inc.* litigation (D. Mass. Civil Action No. 06-CV-11564).
Declaration of Gregory S. Haas (Plaintiff's Exhibit 88 in Haas Deposition), Mar. 13, 2003, *Thierry Pourchez and Bard Access Systems, Inc. v. Diatek, Inc. and Arrow International, Inc.*, Civil Action No. 03-CV-0972 (S.D.N.Y.).
Defendant's Exhibits DX78-DX114, *Thierry Pourchez and Bard Access Systems, Inc. v. Diatek, Inc. and Arrow International, Inc.*, Civil Action No. 03-CV-0972 (S.D.N.Y.), 2003.
Defendants' Reponses and Objections to Plaintiffs' Second Set of Interrogatories (Excerpt), *Thierry Pourchez and Bard Access Systems, Inc. v. Diatek, Inc. and Arrow International, Inc.*, Civil Action No. 03-CV-0972 (S.D.N.Y.) (Oct. 8, 2003).
Delmore et al., "Experience with the Groshong Long-Term Central Venous Catheter", Gynecologic Oncology 34, 216-218 (1989).
Dialysis Vascular Access, SchonXL® Temporary Dialysis (AngioDynamics Inc.) brochure, Nov. 1998.
Dialysis Vascular Access, Technological Innovations Improving Flow (AngioDynamics Inc.) Brochure, 4 pages, Nov. 1998.
Difiore, "Central Venous Dialysis Catheter Evaluatio in Swine", Journal of Vascular Access Devices, Fall 2000.
Donaldson, et al., Peripherally Inserted Central Venous Catheters: US-guided Vascular Access in Pediatric Patients1, Radiology, 1995, vol. 197, pp. 542-544.
Dunea, et. al., A Survey of Permanent Double Lumen Catheters in Hemodialysis Patients. ASAIO Transac. 1991; 37: M276-7.
Dupont et al, Long-term development of Permacath Quinton catheters used as a vascular access route for extra-renal detoxification; Néphrologie, vol. 15, pp. 105-110, 1994.
EP 04712925.9 filed Feb. 19, 2004 Office Action dated Nov. 7, 2008.
EP 08839196.6 filed Oct. 2, 2008 Examination Report dated Jan. 16, 2013.
EP 08839196.6 filed Oct. 2, 2008 Search Opinion dated Jul. 12, 2011.
EP 08839196.6 filed Oct. 2, 2008 Search Report dated Jul. 12, 2011.
EP 08872340.8 filed Oct. 2, 2008 Extended European Search Report and an Opinion dated Apr. 19, 2012.
Gallichio, et al., Placement of a Double Lumen Silastic Catheter for Hemodialysis Access Through the Cephalic Vein, Journal of the American College of Surgeons, 1994, vol. 179, pp. 171-172.
Gravenstein, et al., In Vitro Evaluation of Relative Perforating Potential of Central Venous Catheters: Comparison of Materials, Selected Models, Number of Lumens, and Angles of Incidence to Simulated Membrane, Journal of Clinical Monitoring, 1991, vol. 7, pp. 1-6.
Haindl, H., Technical complications of port-catheter systems, Reg. Cancer Treat, 1989, 2:238-242.
U.S. Appl. No. 10/842,586, filed May 10, 2004 Non-Final Office Action dated Jan. 7, 2008.
U.S. Appl. No. 10/842,586, filed May 10, 2004 Non-Final Office Action dated Jun. 16, 2009.
U.S. Appl. No. 10/842,586, filed May 10, 2004 Non-Final Office Action dated Nov. 13, 2008.
U.S. Appl. No. 10/842,586, filed May 10, 2004 Non-Final Office Action dated Nov. 23, 2009.
U.S. Appl. No. 10/874,298, filed Jun. 9, 2004 Advisory Action dated Feb. 19, 2009.
U.S. Appl. No. 10/874,298, filed Jun. 9, 2004 Final Office Action dated Jul. 15, 2008.
U.S. Appl. No. 10/874,298, filed Jun. 9, 2004 Final Office Action dated Jul. 7, 2010.
U.S. Appl. No. 10/874,298, filed Jun. 9, 2004 Non-Final Office Action dated Aug. 1, 2013.
U.S. Appl. No. 10/874,298, filed Jun. 9, 2004 Non-Final Office Action dated Aug. 18, 2011.
U.S. Appl. No. 10/874,298, filed Jun. 9, 2004 Non-Final Office Action dated Dec. 30, 2009.
U.S. Appl. No. 10/874,298, filed Jun. 9, 2004 Non-Final Office Action dated Feb. 2, 2011.
U.S. Appl. No. 10/874,298, filed Jun. 9, 2004 Non-Final Office Action dated Jul. 23, 2009.
U.S. Appl. No. 10/874,298, filed Jun. 9, 2004 Non-Final Office Action dated May 23, 2006.
U.S. Appl. No. 10/874,298, filed Jun. 9, 2004 Non-Final Office Action dated May 24, 2007.
U.S. Appl. No. 11/859,106, filed Sep. 21, 2007 Final Office Action dated Sep. 1, 2009.
U.S. Appl. No. 11/859,106, filed Sep. 21, 2007 Non-Final Office Action dated Feb. 5, 2009.
U.S. Appl. No. 11/859,106, filed Sep. 21, 2007 Non-Final Office Action dated Mar. 30, 2011.
U.S. Appl. No. 11/859,106, filed Sep. 21, 2007 Non-Final Office Action dated Jun. 25, 2008.
U.S. Appl. No. 11/874,447, filed Oct. 18, 2007 Decision on Appeal dated Dec. 26, 2012.
U.S. Appl. No. 11/874,447, filed Oct. 18, 2007 Examiner's Answer dated Apr. 28, 2010.
U.S. Appl. No. 11/874,447, filed Oct. 18, 2007 Final Office Action dated Jul. 22, 2009.
U.S. Appl. No. 11/874,447, filed Oct. 18, 2007 Non-Final Office Action dated Jan. 6, 2009.
U.S. Appl. No. 11/874,447, filed Oct. 18, 2007 Non-Final Office Action dated Jul. 12, 2013.
U.S. Appl. No. 11/874,447, filed Oct. 18, 2007 Non-Final Office Action dated Jul. 9, 2008.
U.S. Appl. No. 12/048,871, filed Mar. 14, 2008 Examiner's Answer dated Feb. 9, 2012.

(56) References Cited

OTHER PUBLICATIONS

U.S. Appl. No. 12/048,871, filed Mar. 14, 2008 Final Office Action dated Jan. 20, 2011.
U.S. Appl. No. 12/048,871, filed Mar. 14, 2008 Non-Final Office Action dated Jan. 7, 2010.
U.S. Appl. No. 12/048,871, filed Mar. 14, 2008 Non-Final Office Action dated Jul. 7, 2010.
U.S. Appl. No. 12/048,871, filed Mar. 14, 2008 Non-Final Office Action dated May 12, 2009.
U.S. Appl. No. 12/244,514, filed Oct. 2, 2008 Final Office Action dated Jun. 19, 2012.
U.S. Appl. No. 12/244,514, filed Oct. 2, 2008 Non-Final Office Action dated Jan. 17, 2012.
U.S. Appl. No. 12/244,559, filed Oct. 2, 2008 Examiner's Answer dated Mar. 27, 2013.
U.S. Appl. No. 12/244,559, filed Oct. 2, 2009 Final Office Action dated Jul. 3, 2012.
U.S. Appl. No. 12/244,559, filed Oct. 2, 2009 Non-Final Office Action dated Mar. 14, 2012.
U.S. Appl. No. 12/244,514, filed Oct. 2, 2008 Advisory Action dated Sep. 5, 2012.
U.S. Appl. No. 12/244,514, filed Oct. 2, 2008 Final Office Action dated Jul. 11, 2011.
U.S. Appl. No. 12/244,514, filed Oct. 2, 2008 Non-Final Office Action dated Jan. 19, 2011.
U.S. Appl. No. 12/244,544, filed Oct. 2, 2008 Final Office Action dated Jul. 11, 2011.
U.S. Appl. No. 12/244,544, filed Oct. 2, 2008 Non-Final Office Action dated Dec. 22, 2010.
U.S. Appl. No. 12/244,554, filed Oct. 2, 2008 Final Office Action dated Dec. 27, 2010.
U.S. Appl. No. 12/244,554, filed Oct. 2, 2008 Non-Final Office Action dated Jul. 6, 2010.
U.S. Appl. No. 12/253,870, filed Oct. 17, 2008 Non-Final Office Action dated Jan. 21, 2011.
U.S. Appl. No. 12/253,870, filed Oct. 17. 2008 Notice of Allowance dated Aug. 19, 2011.
U.S. Appl. No. 12/262,820, filed Oct. 31, 2008 Non-Final Office Action dated Feb. 18, 2011.
U.S. Appl. No. 12/262,820, filed Oct. 31, 2008 Notice of Allowance dated Sep. 28, 2011.
U.S. Appl. No. 12/263,141, filed Oct. 31, 2008 Advisory Action dated Aug. 17, 2011.
U.S. Appl. No. 12/263,141, filed Oct. 31, 2008 Final Office Action dated May 26, 2011.
U.S. Appl. No. 12/263,141, filed Oct. 31, 2008 Non-Final Office Action dated Jan. 5, 2011.
U.S. Appl. No. 12/414,467, filed Mar. 30, 2009 Final Office Action dated Feb. 7, 2012.
PCT/US15/40463 filed Jul. 14, 2015 International Search Report and Written Opinion dated Dec. 18, 2015.
U.S. Appl. No. 12/048,871, filed Mar. 14, 2008 Final Office Action dated Jan. 4, 2016.
U.S. Appl. No. 12/048,871, filed Mar. 14, 2008 Non-Final Office Action dated Jul. 16, 2015.
U.S. Appl. No. 12/244,559, filed Oct. 2, 2008 Decision on Appeal dated Aug. 31, 2015.
U.S. Appl. No. 14/252,567, filed Apr. 14, 2014 Notice of Allowance dated Sep. 3, 2015.
U.S. Appl. No. 14/328,541, filed Jul. 10, 2014 Final Office Action dated Oct. 22, 2015.
CN 201310073124.8 filed Mar. 7, 2013 First Office Action dated May 5, 2014.
Lubrizol, "Lubrizol's Family of TPUs" Brochure (2005), 9 pages.
PCT/US2014/066811 filed Nov. 21, 2014 International Search Report and Written Opinion dated Apr. 15, 2015.
U.S. Appl. No. 10/874,298, filed Jun. 9, 2004 Final Office Action dated Mar. 18, 2014.
U.S. Appl. No. 10/874,298, filed Jun. 9, 2004 Non-Final Office Action dated Jul. 9, 2014.
U.S. Appl. No. 11/874,447, filed Oct. 18, 2007 Notice of Allowance dated Apr. 18, 2014.
U.S. Appl. No. 12/048,871, filed Mar. 14, 2008 Decision on Appeal dated Feb. 2, 2015.
U.S. Appl. No. 13/294,941, filed Nov. 11, 2011 Notice of Allowance dated Nov. 27, 2013.
U.S. Appl. No. 13/329,156, filed Dec. 16, 2011 Non-Final Office Action dated May 16, 2014.
U.S. Appl. No. 13/897,292, filed May 17, 2013 Final Office Action dated Apr. 9, 2015.
U.S. Appl. No. 13/897,292, filed May 17, 2013 Non-Final Office Action dated Nov. 20, 2014.
U.S. Appl. No. 14/032,858, filed Sep. 20, 2013 Final Office Action dated Mar. 31, 2015.
U.S. Appl. No. 14/032,858, filed Sep. 20, 2013 Non-Final Office Action dated Nov. 4, 2014.
U.S. Appl. No. 14/032,858, filed Sep. 20, 2013, Notice of Allowance dated Jun. 26, 2015.
U.S. Appl. No. 14/252,567, filed Apr. 14, 2014 Non-Final Office Action dated Mar. 31, 2015.
U.S. Appl. No. 14/328,541, filed Jul. 10, 2014 Non-Final Office Action dated Apr. 9, 2015.
U.S. Appl. No. 13/294,941, filed Nov. 11, 2011 Non-Final Office Action dated May 27, 2016.

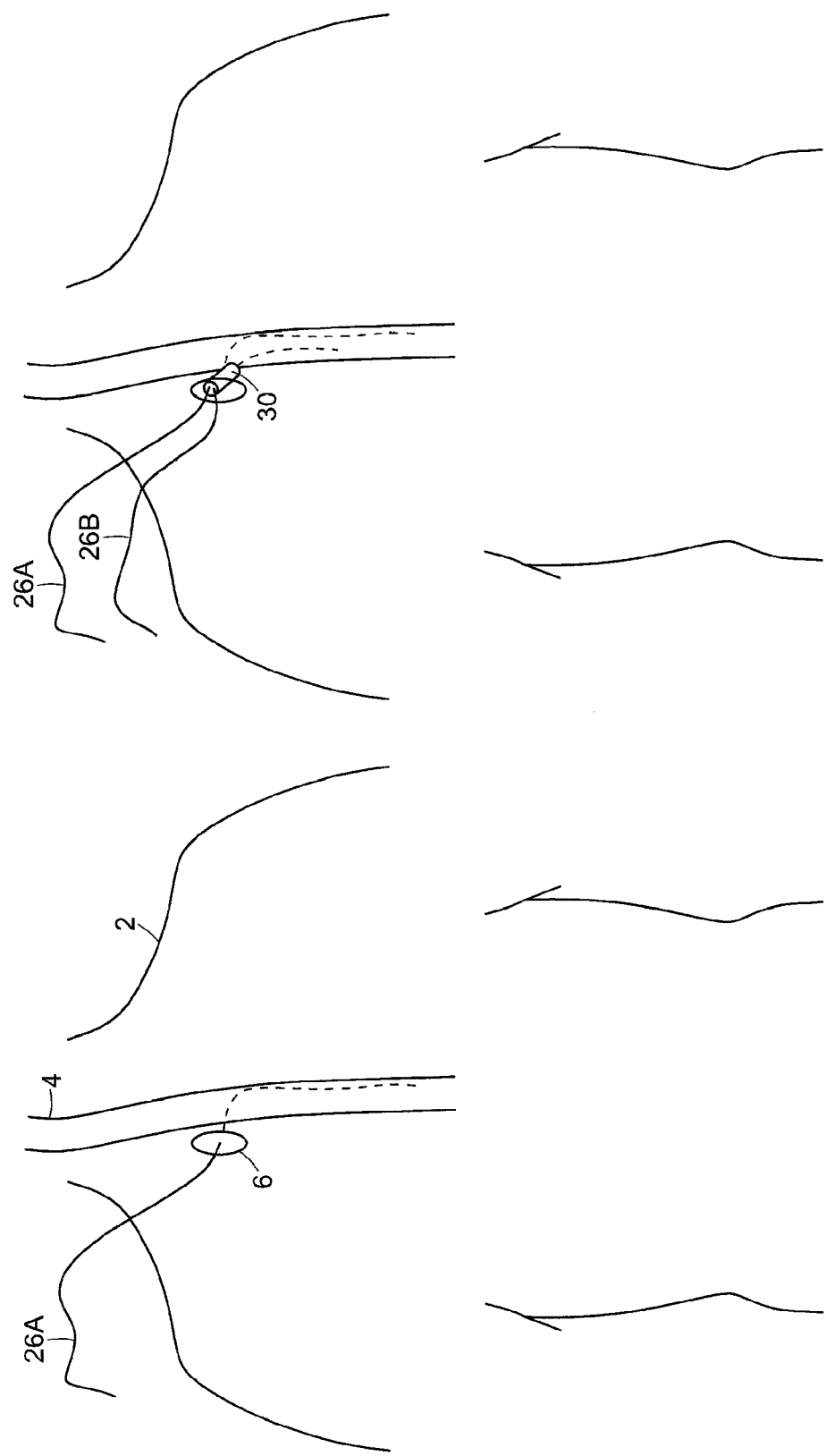

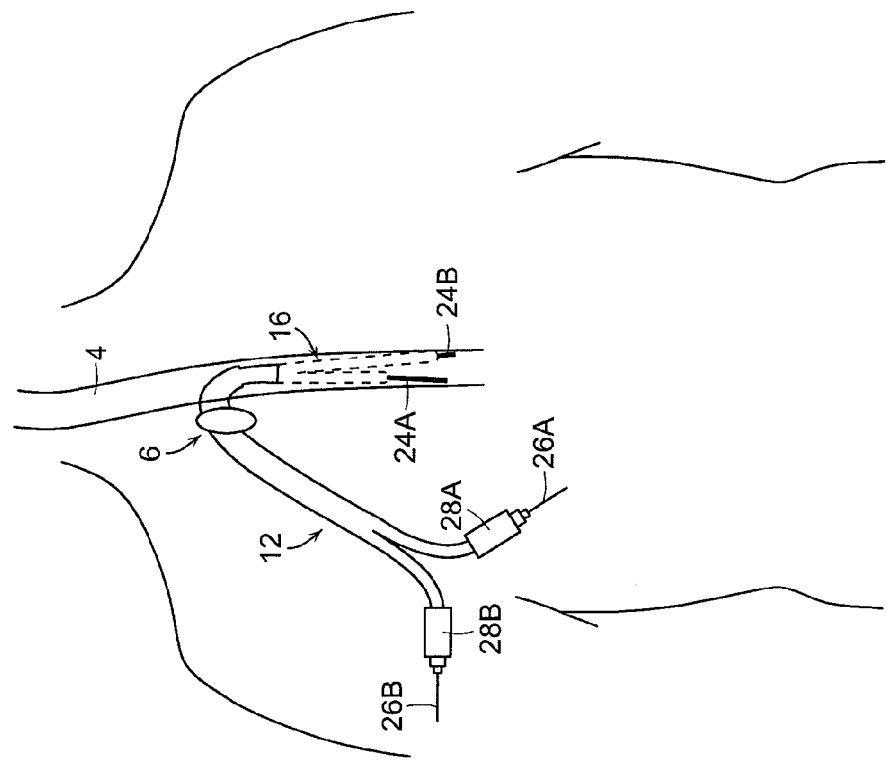
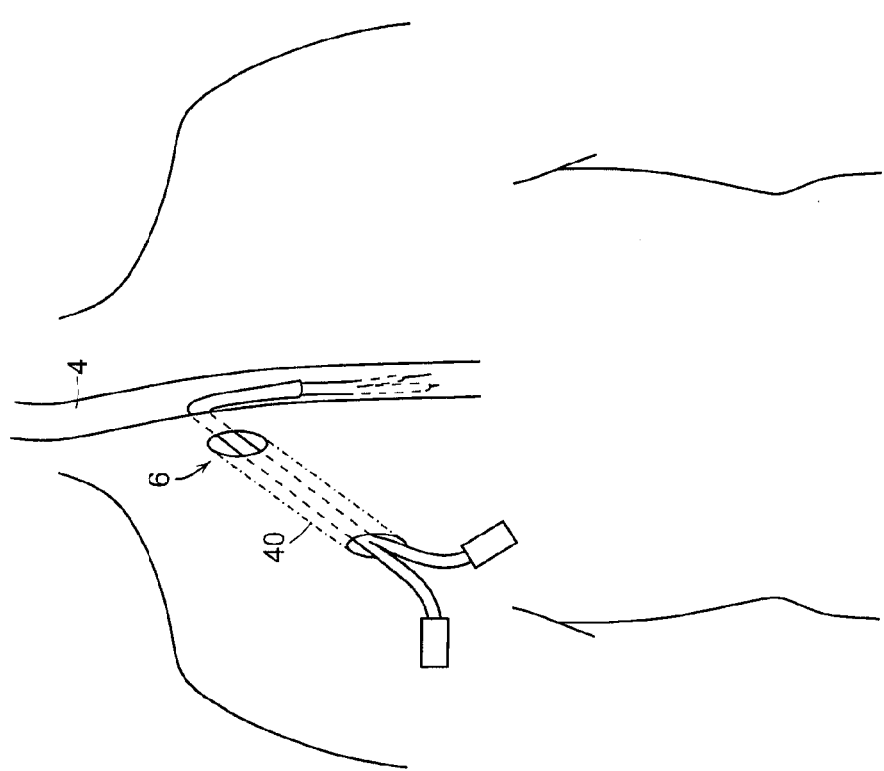

METHODS AND APPARATUS FOR INSERTING MULTI-LUMEN SPLIT-TIP CATHETERS INTO A BLOOD VESSEL

CROSS REFERENCE TO RELATED APPLICATIONS

This application is a division of U.S. patent application Ser. No. 13/445,713, filed Apr. 12, 2012, now U.S. Pat. No. 8,597,275, which is a division of U.S. patent application Ser. No. 12/263,141, filed Oct. 31, 2008, now U.S. Pat. No. 8,206,371, which is a continuation of U.S. patent application Ser. No. 10/445,731, filed May 27, 2003, now abandoned, each of which is hereby incorporated by reference in its entirety into this application.

BACKGROUND OF THE INVENTION

The invention relates to methods and apparatus for inserting a catheter into a body cavity and, more particularly, though not exclusively, to methods and apparatus for inserting a multi-lumen split-tip hemodialysis catheter into a blood vessel for hemodialysis.

Multi-lumen catheters are desirable for various treatment applications such as hemodialysis where fluid extraction and infusion occur simultaneously. These multi-lumen catheters provide a single catheter application having multiple lumen channels each supporting independent flow, thus precluding the need for inserting multiple catheters or multiple-catheter assemblies. Further, because a patient might require frequent dialysis, often only days apart, it is desirable to secure placement of the catheter for extended periods of time. Extended placement, however, requires extreme catheter flexibility to avoid damage to the vessel and permit the catheter to move in the blood flow to minimize the possibility of the catheter remaining in pressure contact with the wall of the vessel for prolonged periods.

Unfortunately, the desired flexibility of these catheters presents insertion difficulties. For example, simply advancing the catheter over a guidewire is very difficult since the catheter lacks sufficient stiffness to slide easily through the vessel wall and into the blood vessel to the desired location. Flexible catheters present additional difficulties associated with subcutaneous tunneling and placement.

Known insertion methods and assemblies attempt to overcome, or at least mitigate, these insertion difficulties by stiffening the catheter temporarily during the insertion process. For example, one known method involves temporarily inserting a rigid tubular applicator into one of the lumens. This permits the stiffened catheter/applicator assembly to be passed over a guidewire into a desired position, at which point the applicator can be removed. For example, U.S. Pat. No. 5,405,341 attempts to solve the problem with a single rigid applicator that is designed for insertion into one lumen but also passes through a portion of the second lumen (at the distal end of the instrument) to effectively stiffen the two lumens of the catheter together during insertion. This approach is cumbersome, at best, and presents additional difficulties in maneuvering the instrument. Further, this temporary rigid applicator approach, however, is poorly suited for placement of a catheter having a split at its distal end into two or more separate lumens (e.g., to further isolate a fluid extraction lumen from a return infusion lumen) because only one tip can be secured.

Hence, there exists a need for better and more effective methods and apparatus for insertion of flexible catheters into vessels.

SUMMARY

The invention provides methods and apparatus for inserting flexible, multi-lumen catheters into blood vessels, and in particular, for inserting flexible, split-tip catheters into blood vessels. The invention accomplishes these objects by temporarily stiffening each catheter lumen and tip independently through use of intra-catheter stiffener elements disposed within the catheter lumens. This provides means for advancing the catheter/stiffeners assembly through a subcutaneous tunnel, and over a plurality of guidewires until a distal portion of the catheter is at a desired position within the vessel.

The intra-catheter stiffener elements are sufficiently stiffening to allow advancing the catheter over guidewires, but also sufficiently flexible to allow bending and looping of the catheter for proper placement within the vessel. Further, the intra-catheter stiffener elements prevent catheter kinking during the insertion process. In one embodiment, the intra-catheter stiffener elements have tapered distal ends which can facilitate entry of the catheter/stiffeners assembly into a blood vessel and/or assist in dilating the blood vessel.

One aspect of the invention provides methods and apparatus for inserting an antegrade tunneled, split-tip, hemodialysis catheter into a blood vessel. A distal portion of each of a plurality of guidewires is disposed in a blood vessel at a first location, generally in proximity to the vessel in which a portion of the catheter is to be placed. A subcutaneous tunnel is formed between the first location and a second location where a proximal end of the catheter can extend from the patient. An intra-catheter stiffener element is inserted into the proximal end of each catheter lumen until it extends beyond the distal end of that catheter lumen. The intra-catheter stiffener element can be releasably coupled, following insertion, to the proximal end of its respective catheter lumen via, for example, a mating luer assembly. Each guidewire can be inserted into to a distal end of a lumen in a respective intra-catheter stiffener element until that guidewire extends from the proximal end of that intra-catheter stiffener element. The catheter can then be advanced over the guidewires and into the blood vessel. Alternatively, the catheter can be advanced over the guidewires until a distal end of the catheter is adjacent to the vessel, at which point the catheter and guidewires can be advanced together into the vessel until the distal end of the catheter is at a desired location therein. Twisting the catheter while simultaneously advancing it along the guidewires can facilitate placement of the catheter into the vessel.

In another aspect, the methods and apparatus of the invention provide for inserting a retrograde tunneled hemodialysis catheter into a blood vessel. A distal portion of each of a plurality of guidewires is inserted into a blood vessel at a first location generally as described above. An intra-catheter stiffener element is placed in each catheter lumen until it extends from a distal end of the catheter, and can be releasably connected to the proximal end of its respective catheter lumen, as noted above. A proximal end of each guidewire is threaded through the distal end of a lumen of each intra-catheter stiffener element until the guidewire extends beyond the proximal end of that stiffener element. The catheter is advanced over the guidewires, optionally using a twisting motion, until a distal portion of the catheter is disposed at a desired location within the vessel, or alternatively, the catheter can be advanced until its distal end is adjacent to the vessel, at which point the catheter and guidewires can be advanced together until the distal end of the catheter is disposed at a desired location within the vessel. The guidewires are removed from the catheter lumens. A subcutaneous tunnel is then formed between the first location and a second location, and the proximal end of the catheter is passed through the first location until it extends from the second location. (If the stiffener elements have not previously been removed, they can be removed from the catheter body following passage of the catheter through the tunnel.) An access port is connected to the proximal end of each of the catheter lumens allowing fluid connection with a treatment device, such as a hemodialysis infuser.

In a related aspect, the methods and kits of the present invention can provide for dilating the desired vessel subsequent to inserting the distal portion of a first guidewire. For example, a size 6-French sheath/dilator can be threaded over the first guidewire. Further guidewires can then be inserted into the expanded vessel, or through a lumen in the sheath and into the vessel. After placement of the guidewires into the vessel, the dilator or sheath can be removed.

In a further related aspect, the methods provide for tunneling between the first and second location by using a pointed stylet. A distal end of a pointed stylet can be inserted through the skin at the second location and pushed toward the first location until the distal end extends therefrom. The distal end of the catheter is removably attached to a proximal end of the stylet. The stylet is then pulled from the first location until the distal end of the catheter extends therefrom, to facilitate an antegrade tunneled catheter.

Alternatively, a pointed distal end of a stylet can be inserted through the skin at the first location and pushed until it extends from the second location. The proximal end of the catheter can be removably attached to the proximal end of the stylet. The stylet is then pulled back toward the second location until the proximal end of the catheter extends therefrom. The catheter is then released from the stylet, thus positioning a retrograde tunneled catheter. To facilitate movement of the catheter within the tunnel, the proximal end of the catheter having mating lures or other coupling features can be removed or severed prior to attachment to the stylet. After tunneling the catheter, fluid couplings or other attachments can be disposed to the proximal end of the lumens.

Preferably, the vessel is expanded to accommodate placement of the distal portion of the catheter in the vessel. Vessel dilators of increasing size can be sequentially inserted into the vessel for this purpose. For example, a size 12-French dilator followed by a size 14-French, which is then followed by a size 16-French dilator, can be inserted into the vessel before advancing the catheter along the guidewires. In other embodiments, fewer (or more) dilators of different sizes can be used. Differing size and number of vessel dilators can be used corresponding to the catheter chosen for the desired application. Use of intra-catheter stiffener elements can preclude use of vessel dilators sized larger that the catheter since the stiffener elements and the catheter itself can provide vessel dilation.

Another aspect of the invention provides for apparatus, in the form of a kit, to insert a multi-lumen catheter into a blood vessel. The kit comprises guidewires each adapted to have a distal portion inserted into a blood vessel. A plurality of intra-catheter stiffener elements preferably having tapered distal ends are also provided, each having a lumen extending along its length sized to accommodate a guidewire, and each having an outside diameter sized to be slidably disposed within a lumen of the catheter. The intra-catheter stiffener elements can be provided in one or more predetermined lengths corresponding to a length of a catheter and its lumens selected for a particular use, or can be of the same length. Further, the intra-catheter stiffeners can be provided with mating devices, such as lures, disposed at a proximal end correspond with mating connectors disposed at a proximal end of the catheter lumens.

One or more vessel dilators can also be provided in the kit, each corresponding in size to a particular application. For example, a size 6-French sheath/dilator can be provided to dilate the vessel to accommodate a plurality of guidewires. A size 12-French, 14-French, as well as a size 16-French, dilator can be provided to dilate the vessel to accommodate the distal tip of the catheter.

The present invention is applicable in the field of hemodialysis, among others, for inserting a multi-tip catheter into a blood vessel. The methods and apparatus provide for insertion of a split-tip catheter without using a tearable sheath and avoid the problems associated with prior art approaches of split tip catheter insertion over a single guidewire.

BRIEF DESCRIPTION OF THE INVENTION

These and other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 2 is a schematic illustration of an initial step of a method according to the invention in which a distal portion of a first guidewire is inserted in a vessel;

FIG. 3 is a schematic illustration of another step of the method of the invention in which a blood vessel dilating sheath and a distal portion of a second guidewire are inserted in a vessel;

FIG. 8 shows the catheter of FIG. 7 with the intra-catheter stiffener elements and guidewires removed;

FIG. 9 is a schematic illustration showing a step of a method according to the invention wherein a retrograde catheter is shown having a distal end disposed in a vessel;

DETAILED DESCRIPTION OF THE INVENTION

Figure 1:
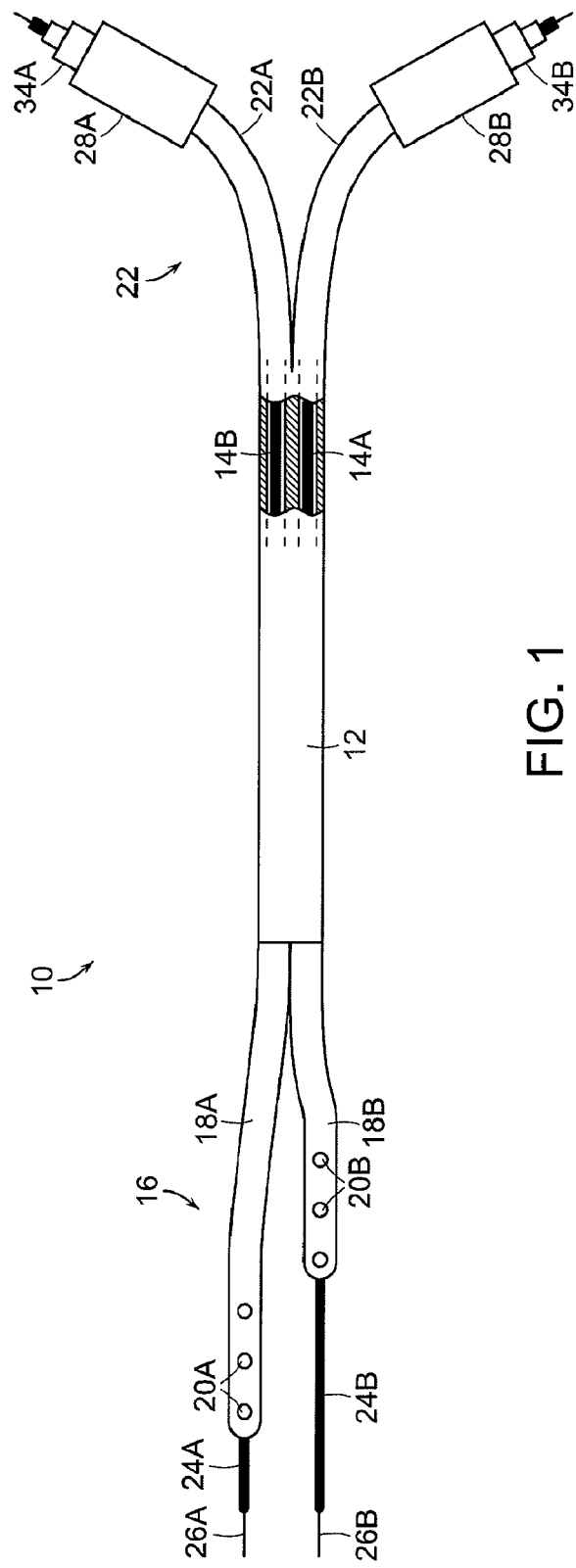
FIG. 1 is a schematic, partially cutaway, side view of a hemodialysis catheter insertion system according to the invention.

In FIG. 1 a catheter system 10 according to the invention is shown having a catheter body 12 with two internal lumens 14A and 14B. The catheter body 12 has a "split-tip" distal end 16 in which the body (and lumens) separate into two distal tip portions, 18A and 18B, which form a single-lumen distal blood removal extension tube and a single-lumen distal blood return extension tube, respectively. The split tips can, but need not have one or more side ports 20A and 20B, in fluid communication with one or the other of the lumens to facilitate blood removal and return, respectively, during hemodialysis. Alternatively, or in conjunction with side ports, the distal ends can be open to provide fluid passageways for blood removal and return. The proximal end 22 of the catheter body can also be split into separate segments 22A and 22B and terminates with two access ports 28A and 28B, which can include couplings 34A and 34B, such luer-locks or the like, to couple the catheter to a hemodialysis machine in which blood is circulated and purified. Proximal segments 22 A and 22 B thus provide a single-lumen proximal blood removal extension tube and a single-lumen proximal blood return extension tube, respectively. The overall system or kit of the invention can also include two intra-catheter stiffener elements 24A and 24B and two guidewires 26A and 26B (shown within the respective lumens 14A and 14B). The catheter body 12 is typically a very flexible silicone, polyurethane or other biocompatible composition (e.g., having a stiffness in the range of about 65 to about 85 durometers). Preferably, the intra-catheter stiffener elements 24A and 24B are composed of a stiffer form of polyethylene or other bio-compatible material. In addition to stiffening the assembly, the stiffener elements can also help to prevent kinking of the catheter during insertion.

The catheter system 10 of FIG. 1 provides for insertion of the distal end of the multi-lumen, split-tip, flexible catheter body 12 into a blood vessel using the intra-catheter stiffener elements and guidewires, as will be explained below. Briefly, a distal portion of each guidewire is disposed at a desired position within the vessel. An intra-catheter stiffener element having a tapered tip to facilitate insertion into the vessel and to provide catheter stiffening is slidably disposed along the length of each catheter lumen until it extends beyond the distal tip of that catheter lumen. A proximal end of each guidewire is threaded through a distal end of a lumen extending along each of the intra-catheter stiffener elements. The catheter is then advanced over the guidewires and into the blood vessel. Alternatively, the catheter can be advanced over the guidewires until the distal end is adjacent to the vessel, at which point the catheter and guidewires can be advanced together into the blood vessel. The guidewires and intra-catheter stiffener elements are then removed from the catheter. The methods and application kit described can be used for any split-tip catheter, and are particularly useful for insertion of subcutaneously tunneled hemodialysis catheters.

A method of insertion according to the invention will next be described in connection with FIGS. 2-8. The procedure involves not only inserting the catheter tips into a blood vessel but also forming a subcutaneous tunnel below a patient's skin to secure the catheter in place and is sometimes described as antegrade or forward insertion. It will be appreciated, however, that the methods described herein can be used for inserting catheter tips into a blood vessel where tunneling is not necessary or desired.

FIG. 2 schematically shows an initial step of a method according to the invention in which a distal portion of a first guidewire 26A is inserted in a vessel 4 of a patient 2. The entry location 6 of the guidewire 26A is referred to herein as the "first location" or the "venotomy site." This first location is typically a surgical incision that provides access to the desired blood vessel which typically includes the internal or external jugular, femoral or subclavian vein, and the vena cava, for example. In one preferred embodiment, the blood vessel chosen for catheter placement can be the right side internal jugular vein.

In FIG. 3, a blood vessel sheath/dilator 30 is shown inserted over the first guidewire 26A to dilate the vessel. The distal portion of a second guidewire 26B is then inserted in the vessel 4 via the sheath/dilator 30.

Figure 4:
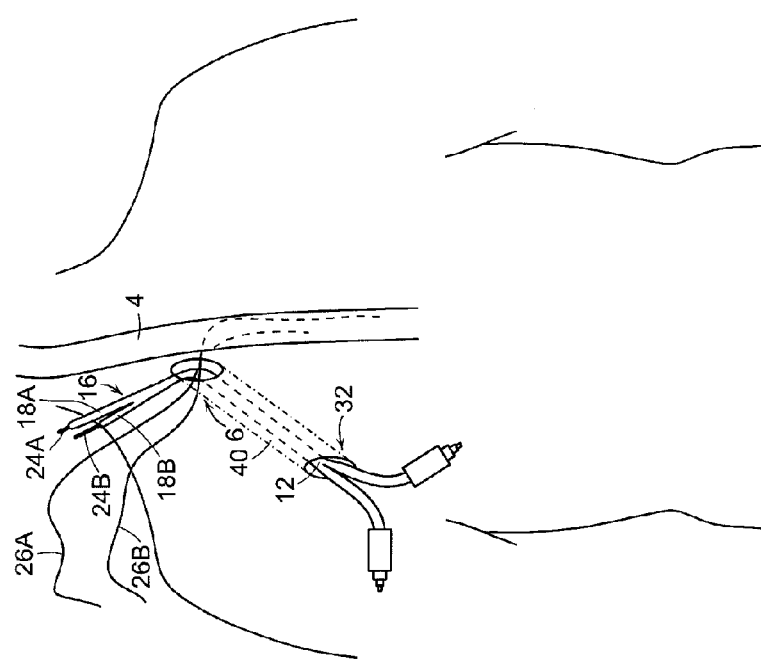
FIG. 4 is a schematic illustration of another step of the method in which an antegrade catheter is disposed in a subcutaneous tunnel between a first location and a second location according to the invention.

With reference to FIG. 4, a subcutaneous tunnel 40 is formed (before or after the insertion of guidewires 26A and 26B) to anchor the catheter body in place and provide two remote ports for coupling the two lumens of the catheter to a dialysis machine. In FIG. 4, a catheter body 12 of an antegrade catheter has been disposed in a subcutaneous tunnel 40 between the first (venous access) location 6 and a second (exit) location 32, such that the distal end of the instrument including the split tips 18A and 18B extend from the first location. Prior to insertion, each of the lumens of catheter body 12 has been fitted with a hollow, tubular, intra-catheter stiffener element or liner, 24A and 24B, respectively.

Figure 5:
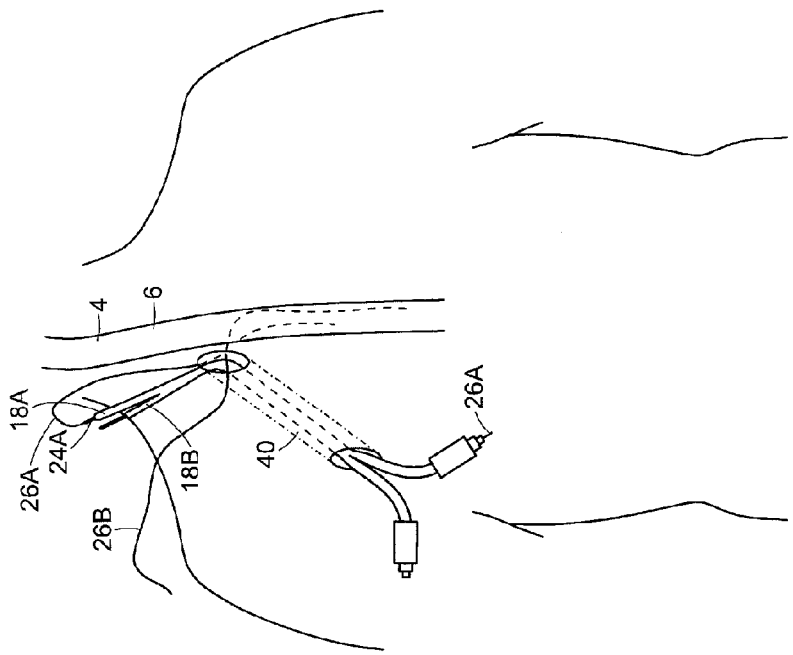
FIG. 5 is a schematic illustration of another step of the method in which the first guidewire is threaded through a first lumen of a catheter assembly according to the invention, in which the catheter assembly has an intra-catheter stiffener element disposed in each lumen of the catheter.
Figure 6:
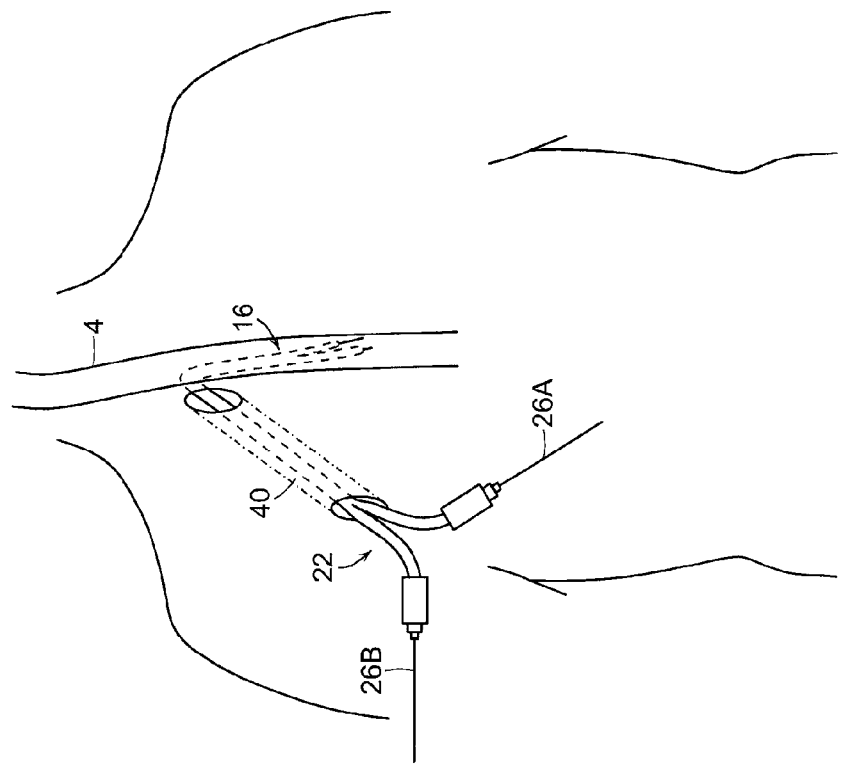
FIG. 6 is a schematic illustration of another step of the method in which the second guidewire is threaded through the second lumen of the catheter assembly to a point where two loops of guidewire remain to facilitate placement of the distal end of the catheter in the vessel.

In FIG. 5, the first guidewire 26A is threaded through a first lumen of the catheter assembly (i.e., through the lumen of intra-catheter stiffener element 24A). In FIG. 6, the second guidewire 26B is threaded through the second lumen of the catheter assembly (i.e., through the lumen of intra-catheter stiffener element 24B). Each of the guidewires is advanced through the catheter assembly to a point where two short loops of guidewire remain to facilitate placement in the vessel.

Figure 7:
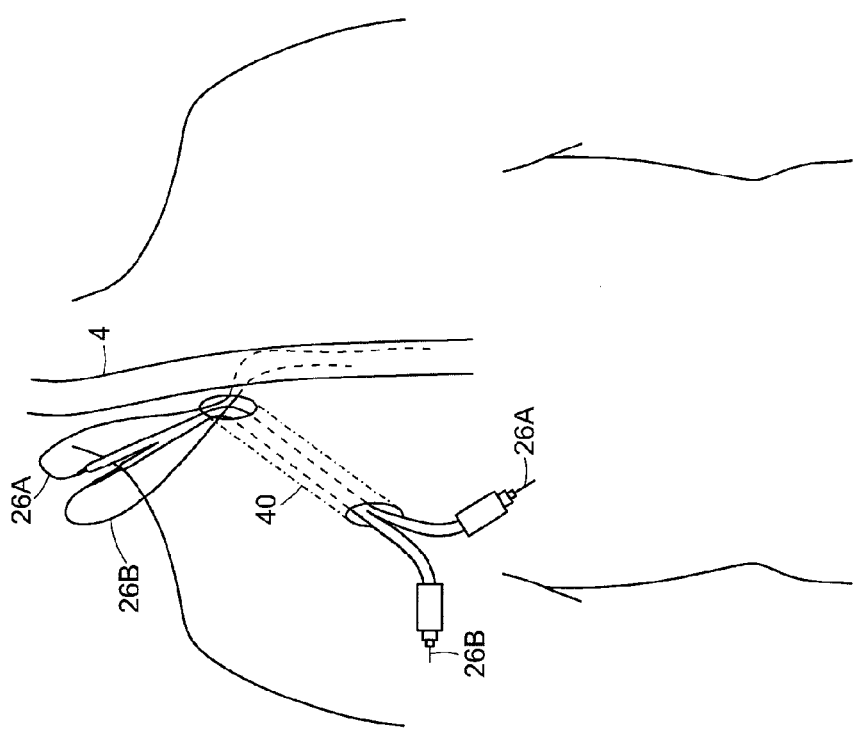
FIG. 7 is a schematic illustration of another step of the method in which the catheter assembly has been advanced along the guidewires until the distal portion of the catheter is positioned within the vessel at a desired location.

As shown in FIG. 7, the catheter assembly is then advanced along the guidewires until the distal end 16 of the catheter is positioned at a desired position within the vessel. In a preferred embodiment, the catheter is advanced over the guidewires until the distal end is adjacent to the vessel, and then the catheter and the guidewires can be advanced together until the distal end of the catheter is positioned at a desired position within the vessel. The guidewires 26A and 26B can then be removed by withdrawing them via the proximal end 22 of the catheter body. Likewise, the intra-catheter stiffener elements 24A and 24B can be removed (either subsequent to the guidewires or at the same time).

Advantageously, this method precludes using a vessel dilator larger than the catheter/stiffeners assembly for placement of the catheter within the vessel since the intra-catheter stiffener elements and the catheter itself provide vessel dilation.

FIG. 8 shows the catheter of FIG. 7 with the intra-catheter stiffener elements and guidewires removed. The venous access incision is then closed and the catheter is secured subcutaneously (e.g., via an implanted cuff and/or sutures).

Although the above detailed description has been presented in connection with an antegrade insertion, it should be clear that the methods and systems of the present invention are equally useful in retrograde or reverse insertions (where the catheter body is passed through the subcutaneous tunnel from venotomy site to the remote exit location).

Thus, a method according to the invention for insertion of a retrograde catheter will next be described. An initial step for insertion of a retrograde catheter begins with placement of guidewires within the vessel as described above in connection with FIGS. 2 and 3.

FIG. 9 illustrates a step of the method wherein the catheter body 12 has each of the lumens fitted with a hollow, tubular, intra-catheter stiffener element or liner, 24A and 24B, respectively. The intra-catheter stiffener elements can have a coupler at a proximal end that releasably couple to a mating coupler at a proximal end of the respective catheter lumen. Guidewires 26A and 26B are threaded through the lumens of the catheter assembly as described above in FIGS. 5 and 6. The catheter body is advanced along the guidewires until the distal end of the catheter in a desired location within the vessel. Alternatively, the catheter body can be advanced along the guidewires until the distal end is adjacent to the vessel, and then the catheter and the guidewires can be advanced until the distal end is located at a desired position within the vessel. The guidewires and, optionally, the intra-catheter stiffener elements are then removed from the lumens.

Figure 10:
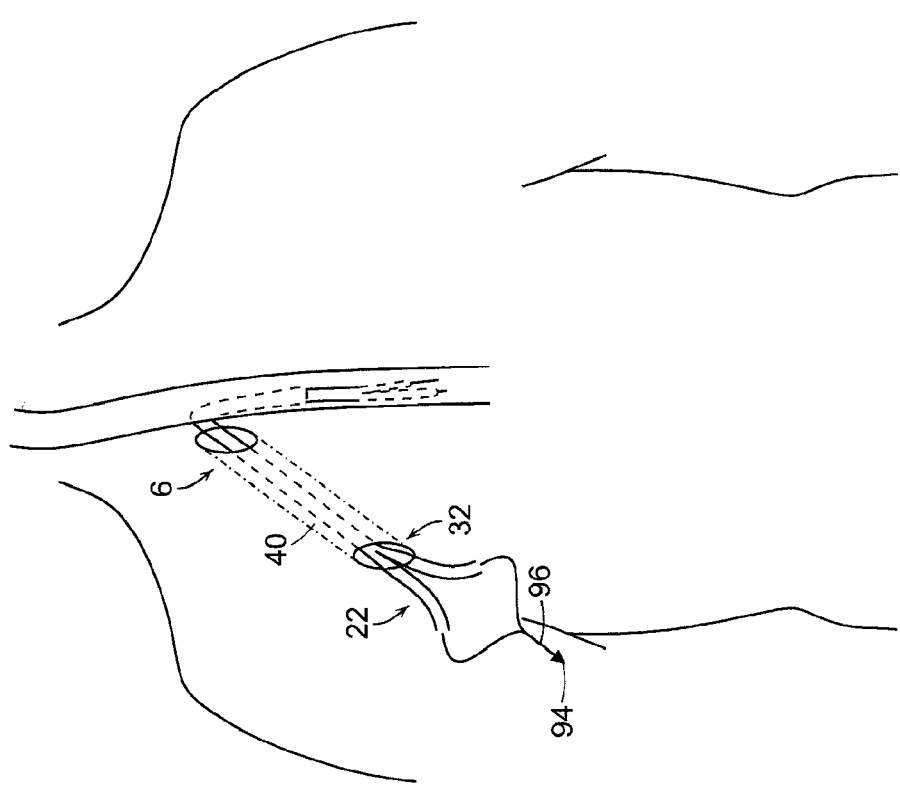
FIG. 10 is a schematic illustration showing a further step of the method wherein the catheter has been subcutaneously tunneled subsequent.

FIG. 10 shows a step of the method wherein the catheter has been subcutaneously tunneled. A subcutaneous tunnel is formed between a second location 32 (exit location) and the first location 6 (venotomy site). Tunneling between the first and second location by using a pointed stylet or trocar 94. Couplers at the proximal end 22 of the catheter lumens are removed, or alternatively, severed therefrom to allow the proximal end of the catheter to be pulled through the tunnel 40. In one embodiment, the proximal end of the catheter is pulled through subcutaneous tunnel from the first location until it extends from the second location. In this embodiment, a pointed distal end of a stylet 94 can be inserted through the skin at the first location and pushed until it extends from the second location. The proximal end of the catheter can be removably attached to the proximal end of the stylet using connector 96. The stylet is then pulled back toward the second location until the proximal end of the catheter extends therefrom.

Figure 11:
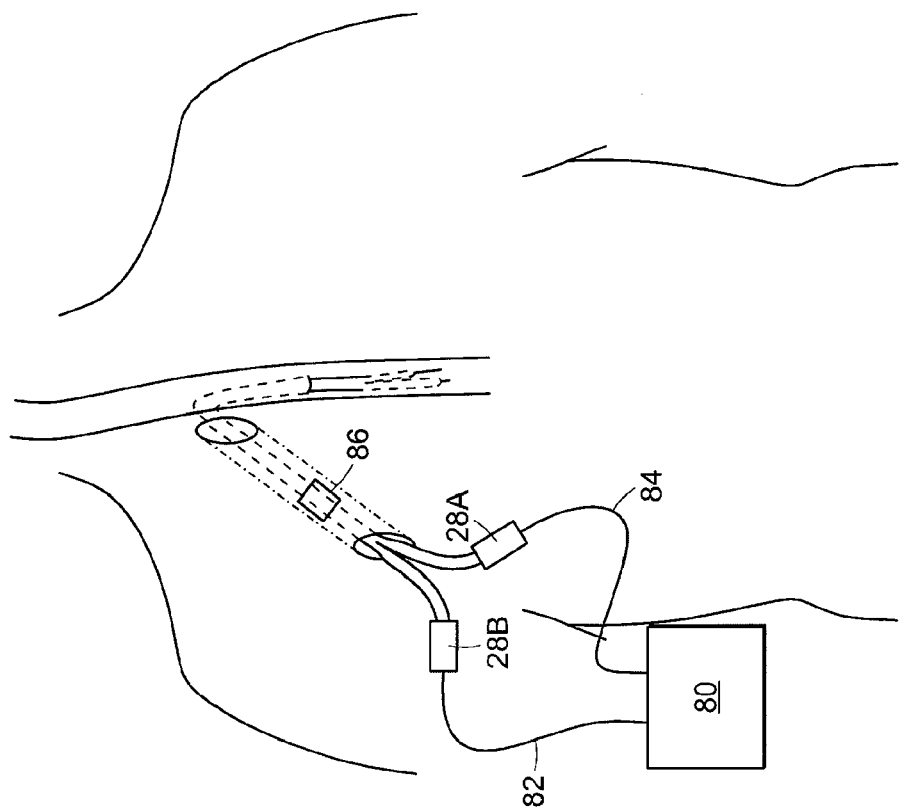
FIG. 11 shows the catheter with fluid-couplers installed.

FIG. 11 illustrates the catheter after tunneling with access ports 28A and 28B installed, or alternatively, replaced and coupled to a hemodialysis machine 80 through legs 82, 84 for blood purification.

As noted above, it will be appreciated that the use of the intra-catheter stiffener elements provide sufficient stiffness so that the flexible split tips can be slid over the guidewires into the desired position with less effort and reduced likelihood of trauma. Catheter kinking is mitigated during the insertion process, thus reducing complexity of catheter insertion.

Figure 12:
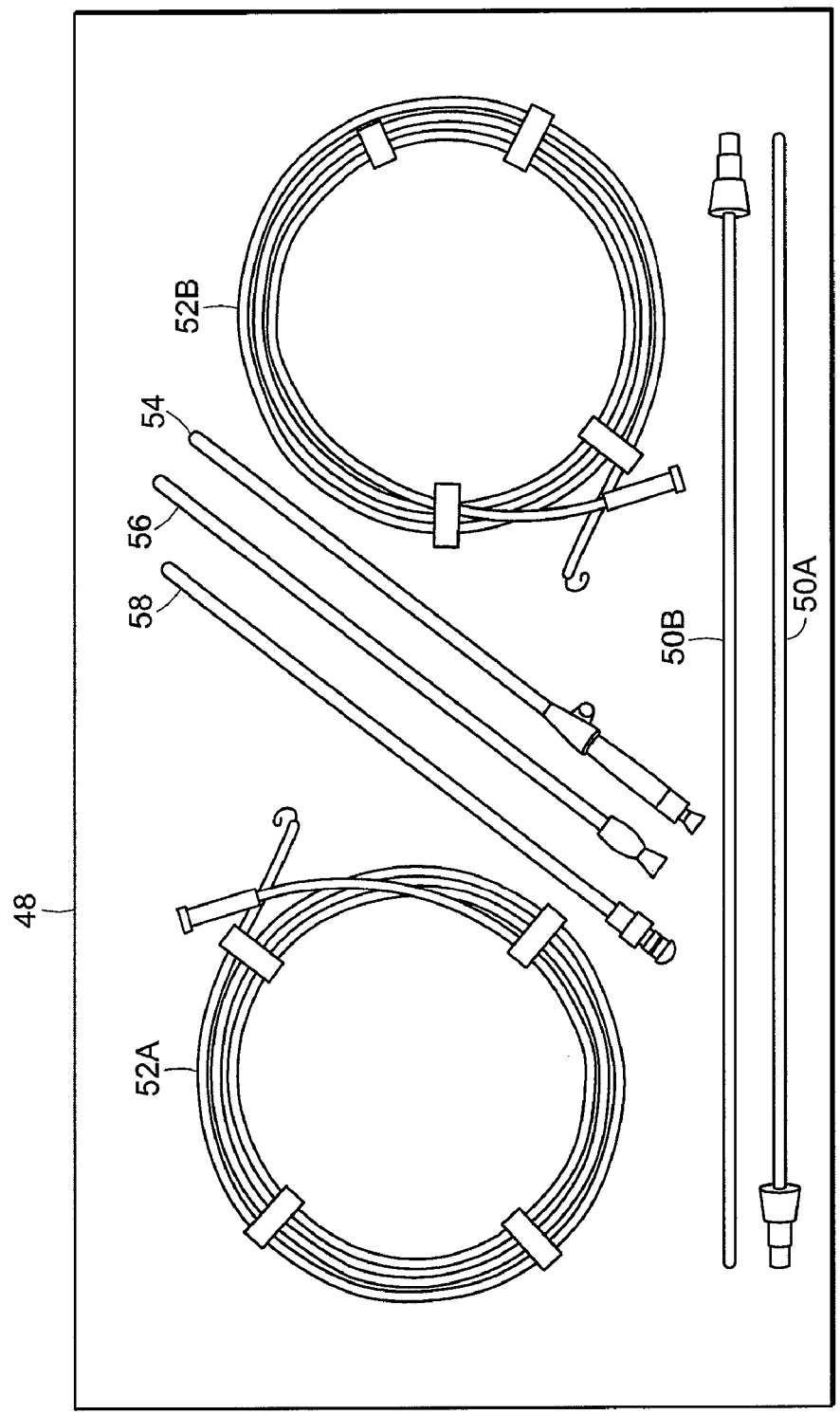
FIG. 12 shows a kit according to the invention for installing catheters such as those described above.

FIG. 12 shows contents of a preferred embodiment of a kit 48 providing equipment to perform the above described methods. Illustrated are two intra-catheter stiffener elements 50A and 50B, two guidewires 52A and 52B, a 6-French sheath/dilator 54 and two vessel dilators of differing sizes 56 and 58. It will be appreciated by one skilled in the art that other arrangements are contemplated, each having at least two intra-catheter stiffener elements. For example, in one embodiment, the insertion kit has a split-tip catheter and two intra-catheter stiffener elements. The kit is suitable for insertion of either antegrade or retrograde catheter configurations according to the illustrated methods described above.

Intra-catheter stiffener elements 50A and 50B are illustrated as 5-French in size and of the same length. However, intra-catheter stiffener elements 50 need not be of the same size and length, but can be selected according to the size and length of the catheter to be inserted. Further, intra-catheter stiffener elements need not have a round exterior shape, but rather, can have an external shape according to the size and shape of an interior of a catheter lumen, for example, oval shaped. In a preferred embodiment, each intra-catheter stiffener element has a tapered configuration along a distal portion to aid in dilating the catheter lumen, with a releasable coupler at a proximal end such as a luer-coupler at a proximal end. Each has a hollow bore or lumen running along its length sized to slidably receive a guidewire as described above. Each preferably has stiffness sufficient to prevent the catheter from kinking or otherwise distorting during the insertion procedure. It will be appreciated that the intra-catheter stiffener elements can be in kit form as separate from, or disposed within, the catheter lumens.

Guidewires 52A and 52B are illustrated as J-straight 0.038" guidewires, however each can vary according to the application and catheter configuration. Each can have a removable sheath to accommodate handling and facilitate placement within a desired location such as a vein.

Sheath/dilator 54 is illustrated as size 6-French, however, other sizes may be used to puncture a wall of a vessel and accommodate one or more guidewires. Dilators 56 and 58 are illustrated as size 14-French and 16-French, respectively, and are suitable for many catheter insertion procedures. In a preferred embodiment, a size 12-French is provided in addition to or instead of one of the illustrated dilators.

It will be appreciated, therefore, that the above methods and kits are useful for inserting hemodialysis catheters in a patient, and in general for multi-lumen split-tip catheters intended for other functions where body fluids are extracted and introduced. As such, the invention is not limited to those embodiments described above, but rather, is limited by the claims that follow.

What is claimed is:

1. A catheter assembly, comprising:
a catheter including a first lumen in fluid communication with a first distal opening and a second lumen in fluid communication with a second distal opening;
a first intra-catheter stiffener element configured for disposition through the first lumen to stiffen the first lumen upon insertion of the catheter into a patient such that a distal end thereof is distal to the first distal opening, the first intra-catheter stiffener element including a first guidewire lumen; and
a second intra-catheter stiffener element configured for disposition through the second lumen to stiffen the second lumen upon insertion of the catheter into a patient such that a distal end thereof is distal to the second distal opening, the second intra-catheter stiffener element including a second guidewire lumen.

2. The catheter assembly according to claim 1, wherein the first intra-catheter stiffener element is pre-disposed in the first lumen and the second intra-catheter stiffener element is pre-disposed in the second lumen.

3. The catheter assembly according to claim 1, wherein the distal ends of the first and second intra-catheter stiffener elements are tapered.

4. The catheter assembly according to claim 1, wherein the first intra-catheter stiffener element has an exterior shape that matches a cross-sectional shape of the first lumen and the second intra-catheter stiffener element has an exterior shape that matches a cross-sectional shape of the second lumen.

5. The catheter assembly according to claim 4, wherein the exterior shape of the first intra-catheter stiffener element is round or oval.

6. The catheter assembly according to claim 4, wherein the exterior shape of the second intra-catheter stiffener element is round or oval.

7. The catheter assembly according to claim 1, wherein the first intra-catheter stiffener element has a first length and the second intra-catheter stiffener element has a second length less than the first length.

8. The catheter assembly according to claim 7, wherein the first intra-catheter stiffener element includes a first coupler at a proximal end thereof, and wherein the second intra-catheter stiffener element includes a second coupler at a proximal end thereof.

9. The catheter assembly according to claim 8, wherein the distal end of the first intra-catheter stiffener element is distal to the distal end of the second intra-catheter stiffener element when the first coupler and the second coupler are coupled to the catheter.

10. The catheter assembly according to claim 1, wherein the first intra-catheter stiffener element includes a first coupler at a proximal end thereof, and wherein the second intra-catheter stiffener element includes a second coupler at a proximal end thereof.

11. The catheter assembly according to claim 10, wherein the first coupler of the first intra-catheter stiffener element mates with a first mating coupler at a first proximal opening of the catheter.

12. The catheter assembly according to claim 11, wherein the second coupler of the second intra-catheter stiffener element mates with a second mating coupler at a second proximal opening of the catheter.

\* \* \* \* \*